(12) United States Patent
Zubok et al.

(10) Patent No.: US 8,900,317 B2
(45) Date of Patent: Dec. 2, 2014

(54) STABILIZING PROSTHESIS SUPPORT STRUCTURE

(75) Inventors: Ray Zubok, Midland Park, NJ (US);
Jorge Montoya, Morris Plains, NJ (US);
Timothy A. Hoeman, Morris Plains, NJ (US); John Chernosky, Brick, NJ (US);
Keith A. Roby, Garnerville, NY (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/475,721

(22) Filed: May 18, 2012

(65) Prior Publication Data
US 2012/0310361 A1    Dec. 6, 2012

Related U.S. Application Data

(60) Provisional application No. 61/488,549, filed on May 20, 2011.

(51) Int. Cl.
*A61F 2/38* (2006.01)
*A61F 2/30* (2006.01)

(52) U.S. Cl.
CPC .......... *A61F 2/30734* (2013.01); *A61F 2/389* (2013.01); *A61F 2002/3051* (2013.01); *A61F 2002/30512* (2013.01); *A61F 2002/30616* (2013.01); *A61F 2002/30884* (2013.01); *A61F 2002/3092* (2013.01)
USPC .................................. 623/20.32; 623/20.34

(58) Field of Classification Search
CPC ..................................................... A61F 2/389
USPC ........................................... 623/20.32–20.34
See application file for complete search history.

(56) References Cited

U.S. PATENT DOCUMENTS 2,947,308 A    8/1960 Gorman
3,855,638 A    12/1974 Pilliar
(Continued)

FOREIGN PATENT DOCUMENTS

AU    2004203348 A1    9/2005
CA    2473633 A1    9/2005
(Continued)

OTHER PUBLICATIONS

Restriction Requirement mailed Aug. 25, 2006 in U.S. Appl. No. 10/780,378.
(Continued)

*Primary Examiner* — Jason-Dennis Stewart
(74) *Attorney, Agent, or Firm* — Schwegman Lundberg & Woessner, P.A.

(57) ABSTRACT

A tibial support structure includes a platform portion and a medullary portion that are monolithically formed as a single piece. The medullary and platform portions of the augment component are adapted to accommodate and mechanically attach to a tibial baseplate, and are individually shaped and sized to replace damaged bone stock both within the tibia, as well at the tibial proximal surface. The monolithic formation of the tibial support structure provides a strong and stable foundation for a tibial baseplate and facilitates restoration of the anatomic joint line, even where substantial resections of the proximal tibia have been made. The tibial support structure may be made of a bone-ingrowth material which facilitates preservation and rebuilding of the proximal tibia after implantation, while also preserving the restored joint line by allowing revision surgeries to be performed without removal of the tibial support structure.

22 Claims, 25 Drawing Sheets

(56) References Cited

U.S. PATENT DOCUMENTS

| | | | |
|---|---|---|---|
| 4,064,567 A | 12/1977 | Burstein et al. | |
| 4,136,405 A | 1/1979 | Patrick et al. | |
| 4,206,516 A | 6/1980 | Pilliar | |
| 4,216,549 A | 8/1980 | Hillberry et al. | |
| 4,219,893 A | 9/1980 | Noiles | |
| 4,224,696 A | 9/1980 | Murray et al. | |
| 4,404,691 A | 9/1983 | Buning et al. | |
| 4,444,061 A | 4/1984 | Mathias et al. | |
| 4,523,587 A | 6/1985 | Frey | |
| 4,549,319 A | 10/1985 | Meyer | |
| 4,659,331 A | 4/1987 | Matthews et al. | |
| 4,678,470 A | 7/1987 | Nashef et al. | |
| 4,711,639 A | 12/1987 | Grundei | |
| 4,718,909 A | 1/1988 | Brown | |
| 4,735,625 A | 4/1988 | Davidson | |
| 4,778,473 A | 10/1988 | Matthews et al. | |
| 4,789,663 A | 12/1988 | Wallace | |
| 4,790,852 A | 12/1988 | Noiles | |
| 4,822,366 A | 4/1989 | Bolesky | |
| 4,827,919 A | 5/1989 | Barbarito et al. | |
| 4,878,919 A | 11/1989 | Pavlansky et al. | |
| 4,883,488 A | 11/1989 | Bloebaum et al. | |
| 4,888,021 A | 12/1989 | Forte et al. | |
| 4,944,757 A | 7/1990 | Martinez et al. | |
| 4,950,298 A | 8/1990 | Gustilo et al. | |
| 4,988,359 A | 1/1991 | Frey et al. | |
| 5,019,103 A | 5/1991 | Van Zile et al. | |
| 5,032,134 A | 7/1991 | Lindwer | |
| 5,059,196 A | 10/1991 | Coates | |
| 5,108,446 A | 4/1992 | Wagner et al. | |
| 5,133,771 A | 7/1992 | Duncan et al. | |
| 5,152,797 A | 10/1992 | Luckman et al. | |
| 5,163,966 A | 11/1992 | Norton et al. | |
| 5,197,488 A | 3/1993 | Kovacevic | |
| 5,211,664 A | 5/1993 | Tepic et al. | |
| 5,222,984 A | 6/1993 | Forte | |
| 5,246,459 A | 9/1993 | Elias | |
| 5,356,414 A | 10/1994 | Cohen et al. | |
| 5,356,629 A | 10/1994 | Sanders et al. | |
| 5,358,527 A | 10/1994 | Forte | |
| 5,358,530 A | 10/1994 | Hodorek | |
| 5,370,693 A | 12/1994 | Kelman et al. | |
| 5,376,123 A | 12/1994 | Klaue et al. | |
| 5,387,241 A | 2/1995 | Hayes | |
| 5,405,396 A * | 4/1995 | Heldreth et al. | 623/20.32 |
| 5,413,604 A | 5/1995 | Hodge | |
| 5,462,563 A | 10/1995 | Shearer et al. | |
| 5,480,445 A | 1/1996 | Burkinshaw | |
| 5,489,311 A | 2/1996 | Cipolletti | |
| 5,507,830 A | 4/1996 | DeMane et al. | |
| 5,510,396 A | 4/1996 | Prewett et al. | |
| 5,531,791 A | 7/1996 | Wolfinbarger et al. | |
| 5,549,685 A | 8/1996 | Hayes | |
| 5,591,233 A | 1/1997 | Kelman et al. | |
| 5,609,645 A | 3/1997 | Vinciguerra | |
| 5,658,349 A | 8/1997 | Brooks et al. | |
| 5,683,467 A | 11/1997 | Pappas | |
| 5,734,959 A | 3/1998 | Krebs et al. | |
| 5,766,256 A | 6/1998 | Oudard et al. | |
| 5,782,925 A | 7/1998 | Collazo et al. | |
| 5,788,976 A | 8/1998 | Bradford | |
| 5,824,103 A | 10/1998 | Williams | |
| 5,858,020 A | 1/1999 | Johnson et al. | |
| 5,871,548 A | 2/1999 | Sanders et al. | |
| 5,879,393 A | 3/1999 | Whiteside | |
| 5,910,172 A | 6/1999 | Penenberg | |
| 5,931,409 A | 8/1999 | Nulle et al. | |
| 5,957,979 A | 9/1999 | Beckman et al. | |
| 5,972,368 A | 10/1999 | McKay | |
| 5,976,148 A | 11/1999 | Charpenet et al. | |
| 5,984,968 A | 11/1999 | Park | |
| 5,997,581 A | 12/1999 | Khalili | |
| 6,008,432 A | 12/1999 | Taylor | |
| 6,013,080 A | 1/2000 | Khalili | |
| 6,039,764 A | 3/2000 | Pottenger et al. | |
| 6,053,945 A | 4/2000 | O'Neil et al. | |
| 6,074,423 A | 6/2000 | Lawson | |
| 6,074,424 A | 6/2000 | Perrone et al. | |
| 6,080,195 A | 6/2000 | Colleran et al. | |
| 6,117,175 A | 9/2000 | Bosredon | |
| 6,126,691 A | 10/2000 | Kasra et al. | |
| 6,136,029 A | 10/2000 | Johnson et al. | |
| 6,139,581 A | 10/2000 | Engh et al. | |
| 6,139,584 A | 10/2000 | Ochoa et al. | |
| 6,142,998 A | 11/2000 | Smith et al. | |
| 6,162,254 A | 12/2000 | Timoteo | |
| 6,162,255 A | 12/2000 | Oyola | |
| 6,171,342 B1 | 1/2001 | O'Neil | |
| 6,264,699 B1 | 7/2001 | Noiles | |
| 6,290,725 B1 | 9/2001 | Weiss et al. | |
| 6,355,069 B1 | 3/2002 | DeCarlo et al. | |
| 6,423,096 B1 | 7/2002 | Musset et al. | |
| 6,428,578 B2 | 8/2002 | White | |
| 6,613,092 B1 | 9/2003 | Kana et al. | |
| 6,699,293 B2 | 3/2004 | White | |
| 6,797,006 B2 | 9/2004 | Hodorek | |
| 6,843,806 B2 | 1/2005 | Haves et al. | |
| 6,946,001 B2 | 9/2005 | Sanford et al. | |
| 6,981,991 B2 | 1/2006 | Ferree | |
| 7,105,026 B2 | 9/2006 | Johnson et al. | |
| 7,179,295 B2 | 2/2007 | Kovacevic | |
| 7,291,174 B2 | 11/2007 | German et al. | |
| 7,357,817 B2 * | 4/2008 | D'Alessio, II | 623/20.15 |
| 7,435,263 B2 | 10/2008 | Barnett et al. | |
| 7,892,288 B2 | 2/2011 | Blaylock et al. | |
| 2002/0151984 A1 | 10/2002 | White | |
| 2003/0065397 A1 | 4/2003 | Hanssen et al. | |
| 2003/0183025 A1 | 10/2003 | Krstic | |
| 2003/0229398 A1 | 12/2003 | Iesaka et al. | |
| 2004/0034432 A1 | 2/2004 | Hughes et al. | |
| 2004/0049270 A1 | 3/2004 | Gerwirtz | |
| 2004/0049284 A1 | 3/2004 | German et al. | |
| 2004/0117024 A1 | 6/2004 | Gerbec et al. | |
| 2004/0162619 A1 | 8/2004 | Blaylock et al. | |
| 2005/0107883 A1 | 5/2005 | Goodfried et al. | |
| 2005/0278034 A1 | 12/2005 | Johnson et al. | |
| 2005/0283254 A1 | 12/2005 | Hayes, Jr. et al. | |
| 2007/0088443 A1 | 4/2007 | Hanssen et al. | |
| 2007/0100463 A1 * | 5/2007 | Aram et al. | 623/20.29 |
| 2007/0179627 A1 | 8/2007 | Gustilo et al. | |
| 2008/0114464 A1 * | 5/2008 | Barnett et al. | 623/20.33 |
| 2008/0167722 A1 | 7/2008 | Metzger et al. | |
| 2008/0281430 A1 | 11/2008 | Kelman et al. | |
| 2010/0057212 A1 * | 3/2010 | Thomas | 623/20.32 |
| 2010/0114323 A1 | 5/2010 | Deruntz et al. | |
| 2010/0145452 A1 | 6/2010 | Blaylock et al. | |
| 2011/0009974 A1 | 1/2011 | Blaylock et al. | |
| 2011/0066252 A1 | 3/2011 | Hanssen et al. | |
| 2011/0112651 A1 | 5/2011 | Blaylock et al. | |
| 2011/0295382 A1 | 12/2011 | Hanssen et al. | |
| 2013/0166037 A1 * | 6/2013 | Goodfellow et al. | 623/20.32 |

FOREIGN PATENT DOCUMENTS

| | | |
|---|---|---|
| EP | 0336774 B1 | 12/1992 |
| EP | 0863731 B1 | 9/1998 |
| EP | 0532585 B1 | 4/2000 |
| EP | 1004283 A2 | 5/2000 |
| EP | 1396240 A2 | 3/2004 |
| FR | 2772593 A1 | 6/1999 |
| GB | 2223172 A | 4/1990 |
| JP | 6-169930 A | 6/1994 |
| JP | 10-277069 A | 10/1998 |
| JP | 2000-185062 A | 7/2000 |
| JP | 2001-503283 T | 3/2001 |
| JP | 2001-526573 T | 12/2001 |
| JP | 2004-016822 A | 1/2004 |
| JP | 2005-246036 A | 9/2005 |
| WO | WO97/30661 A1 | 8/1997 |
| WO | WO02/05732 A1 | 1/2002 |
| WO | WO-2012162180 A1 | 11/2012 |

(56) References Cited

OTHER PUBLICATIONS

Election filed Sep. 15, 2006 in U.S. Appl. No. 10/780,378.
Restriction Requirement mailed Dec. 4, 2006 in U.S. Appl. No. 10/780,378.
Election filed Jan. 4, 2007 in U.S. Appl. No. 10/780,378.
Office Action mailed Mar. 30, 2007 in U.S. Appl. No. 10/780,378.
Amendment filed Jun. 15, 2007 in U.S. Appl. No. 10/780,378.
Final Office Action mailed Aug. 27, 2007 in U.S. Appl. No. 10/780,378.
Amendment filed Oct. 31, 2007 in U.S. Appl. No. 10/780,378.
Office Action mailed Dec. 12, 2007 in U.S. Appl. No. 10/780,378.
Amendment filed May 28, 2008 in U.S. Appl. No. 10/780,378.
Final Office Action mailed Aug. 21, 2008 in U.S. Appl. No. 10/780,378.
Amendment filed Nov. 12, 2008 in U.S. Appl. No. 10/780,378.
Office Action mailed Feb. 2, 2009 in U.S. Appl. No. 10/780,378.
Amendment filed Jun. 24, 2009 in U.S. Appl. No. 10/780,378.
Restriction Requirement mailed Oct. 22, 2009 in U.S. Appl. No. 10/780,378.
Election filed Dec. 22, 2009 in U.S. Appl. No. 10/780,378.
Final Office Action mailed Apr. 20, 2010 in U.S. Appl. No. 10/780,378.
Office Action mailed Nov. 2, 2006 in related U.S. Appl. No. 10/794,721.
Amendment filed Feb. 2, 2007 in related U.S. Appl. No. 10/794,721.
Amendment filed May 18, 2007 in related U.S. Appl. No. 10/794,721.
Office Action mailed Aug. 3, 2007 in related U.S. Appl. No. 10/794,721.
Amendment filed Nov. 8, 2007 in related U.S. Appl. No. 10/794,721.
Final Office Action mailed Jan. 16, 2008 in related U.S. Appl. No. 10/794,721.
Amendment filed Jun. 16, 2008 in related U.S. Appl. No. 10/794,721.
Office Action mailed Jul. 8, 2008 in related U.S. Appl. No. 10/794,721.
Amendment filed Oct. 8, 2008 in related U.S. Appl. No. 10/794,721.
Final Office Action mailed Jan. 16, 2009 in related U.S. Appl. No. 10/794,721.
Amendment filed Apr. 14, 2009 in related U.S. Appl. No. 10/794,721.
The Office Action mailed Jun. 15, 2009 in related U.S. Appl. No. 10/794,721.
Amendment filed Sep. 28, 2009 in related U.S. Appl. No. 10/794,721.
Compliant Amendment filed Feb. 8, 2010 in related U.S. Appl. No. 10/794,721.
The Office Action mailed May 6, 2010 in related U.S. Appl. No. 10/794,721.
Amendment filed Oct. 6, 2010 in related U.S. Appl. No. 10/794,721.
The Japanese office action mailed May 26, 2009, in related Japanese Patent Application No. 2004-216179.
Product Brochure—Femoral/Tibial Augmentation Orthopaedic Salvage System, Biomet Orthopedics, Inc., 2003, 2004.
Restriction Requirement mailed Aug. 21, 2009 in related U.S. Appl. No. 11/560,276.
Election filed Oct. 21, 2009 in related U.S. Appl. No. 11/560,276.
Office action mailed Mar. 3, 2010 in related U.S. Appl. No. 11/560,276.
Amendment filed Aug. 2, 2010 in related U.S. Appl. No. 11/560,276.
Office action mailed Oct. 8, 2010 in related U.S. Appl. No. 11/560,276.
Amendment filed Feb. 7, 2011 in related U.S. Appl. No. 11/560,276.
Office action mailed Aug. 11, 2011 n related U.S. Appl. No. 11/560,276.
Amendment filed Feb. 13, 2012 in related U.S. Appl. No. 11/560,276.
Final office action mailed Mar. 27, 2012 in related U.S. Appl. No. 11/560,276.
Amendment filed Jun. 27, 2012 in related U.S. Appl. No. 11/560,276.
International Search Report and Written Opinion mailed Jul. 3, 2012 in International Application No. PCT/US2012/038673 from the International Searching Authority.
International Application Serial No. PCT/US2012/038673, International Preliminary Report on Patentability mailed Nov. 28, 2013, 8 pgs.

* cited by examiner

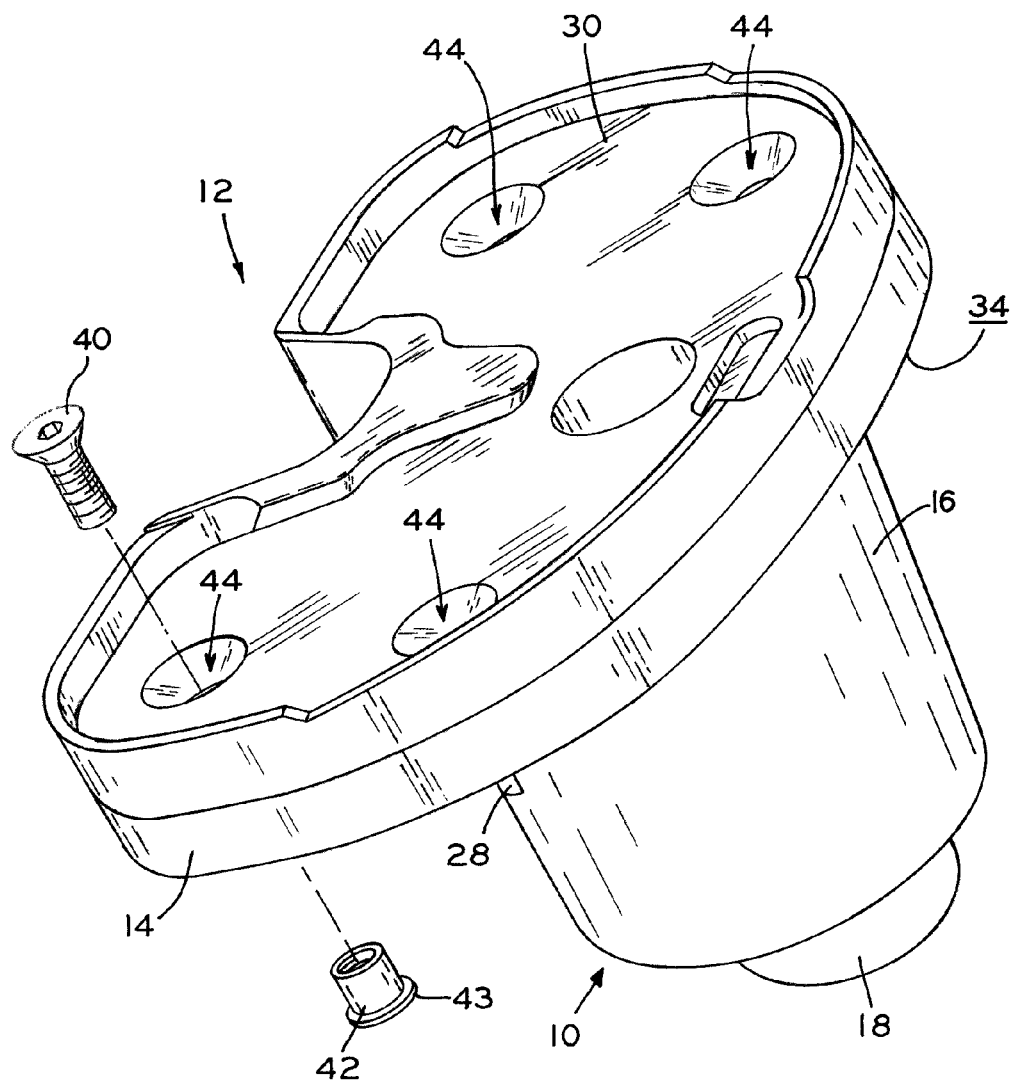
FIG_1A

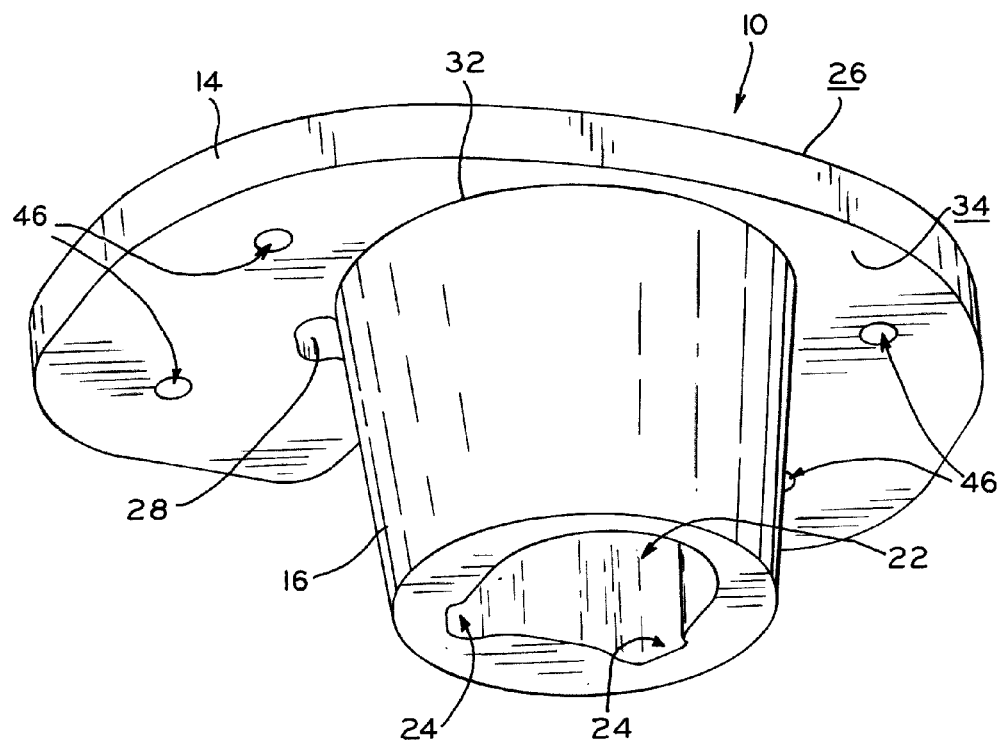
FIG_1B

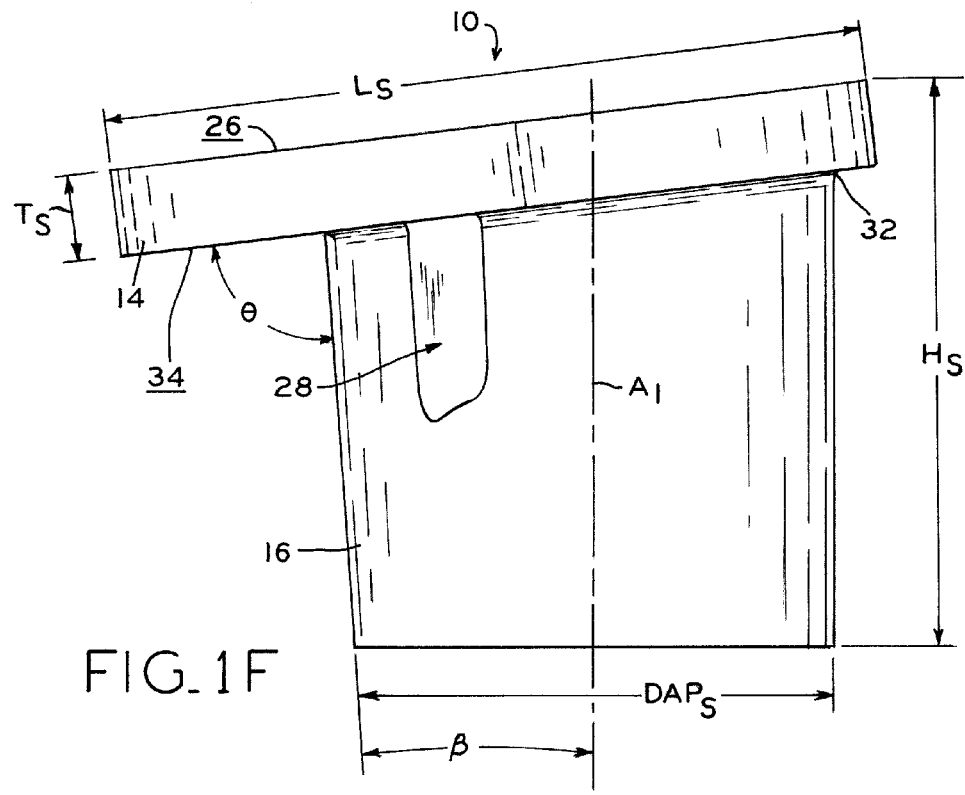
FIG._1F
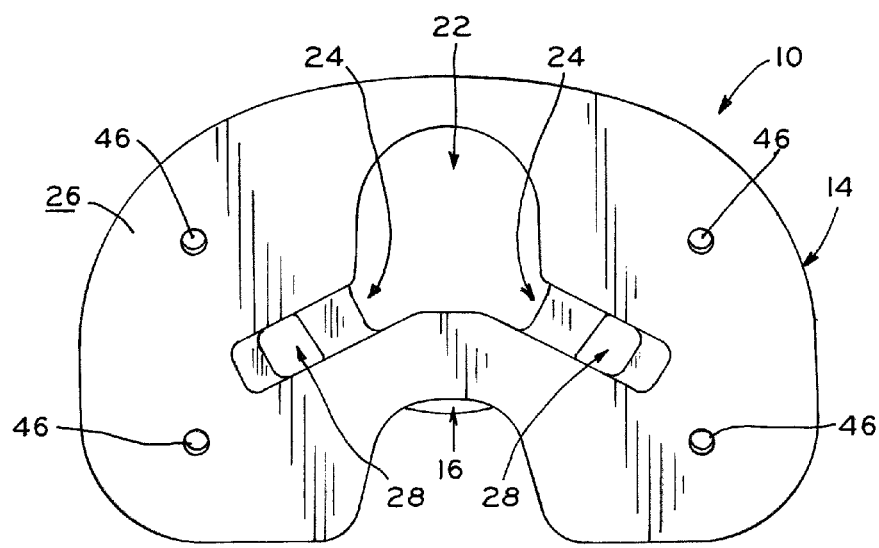
FIG._1G

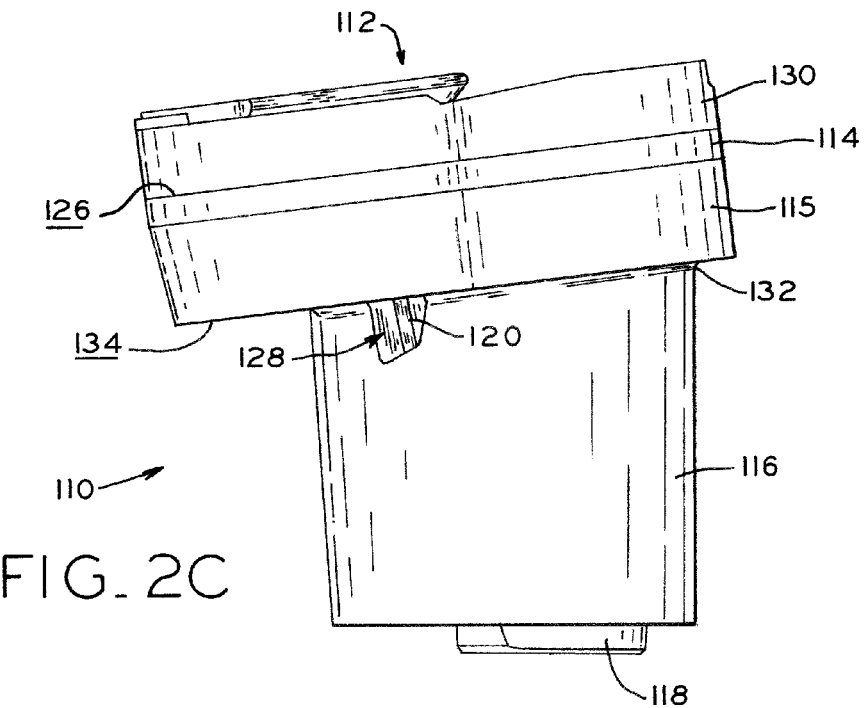
FIG_2C
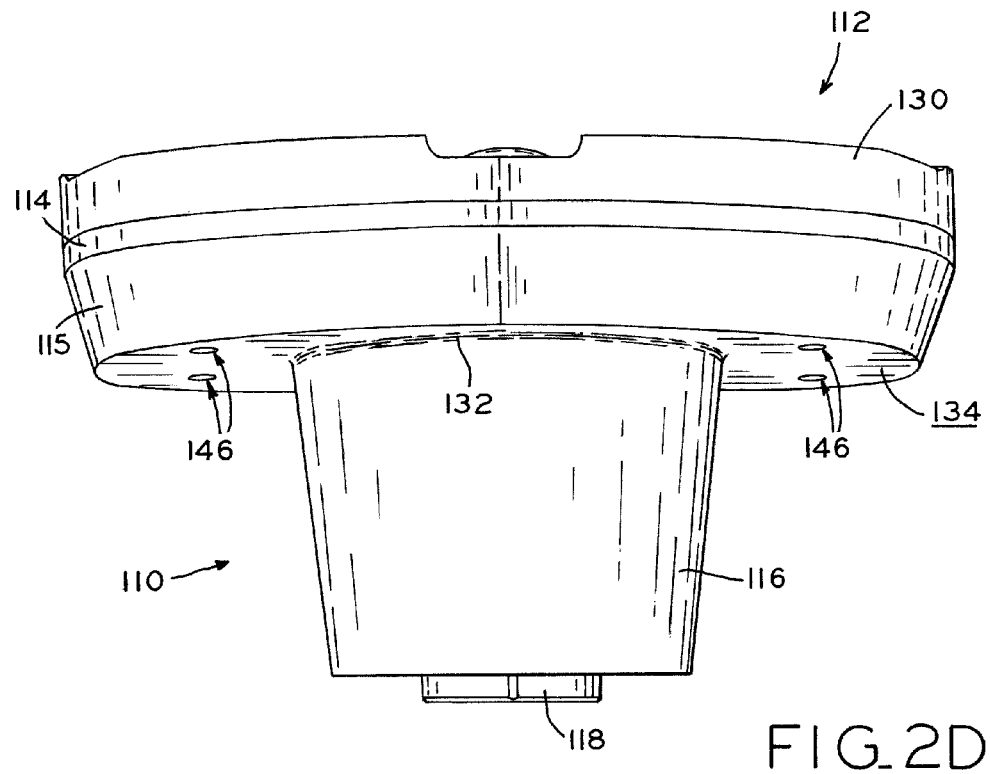
FIG_2D

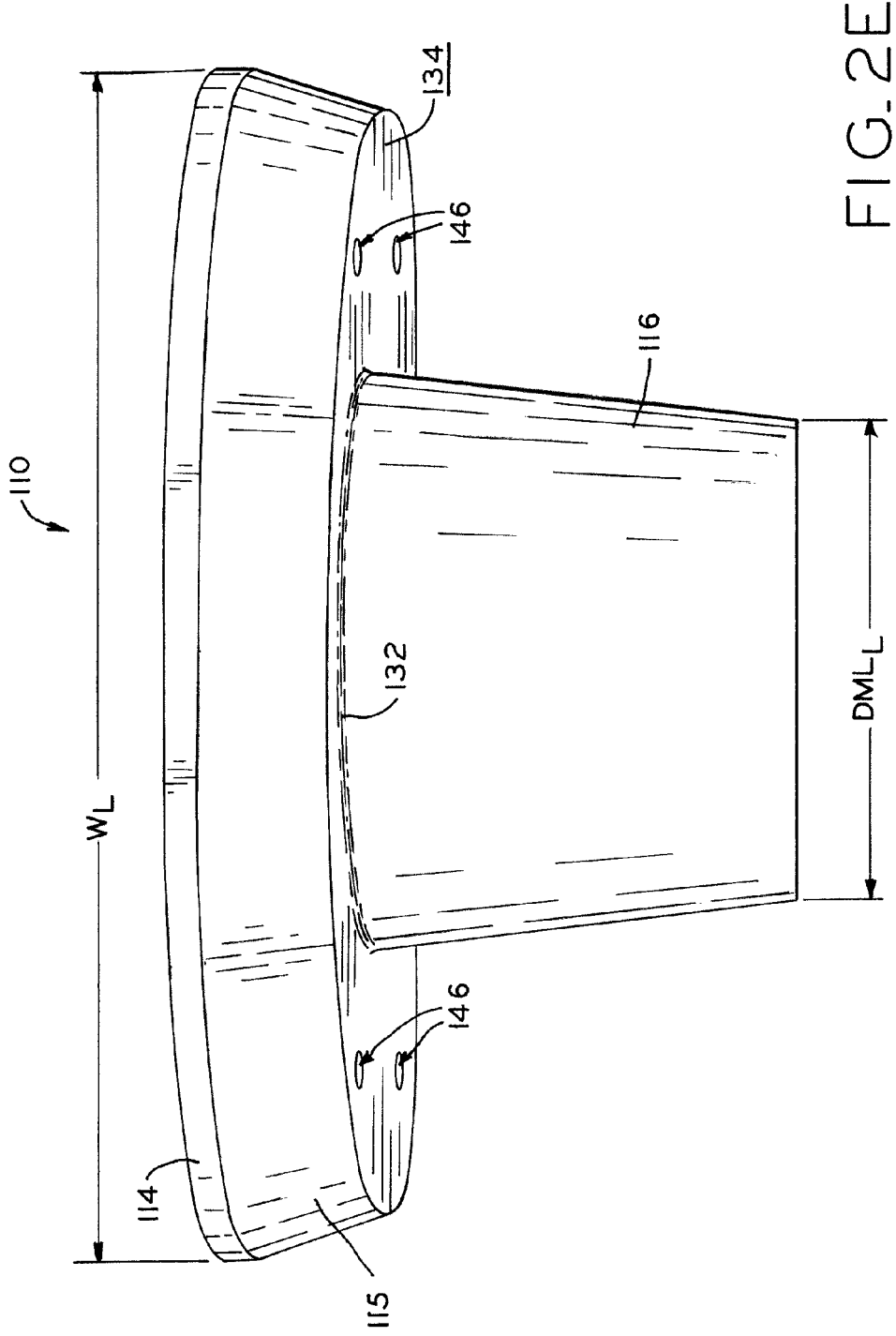

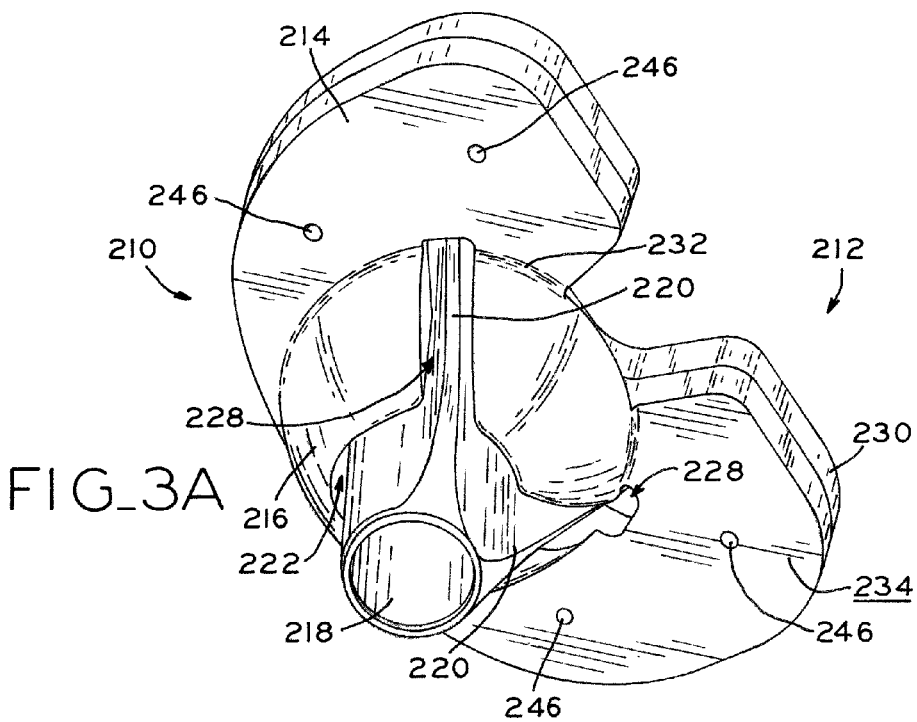
FIG_3A
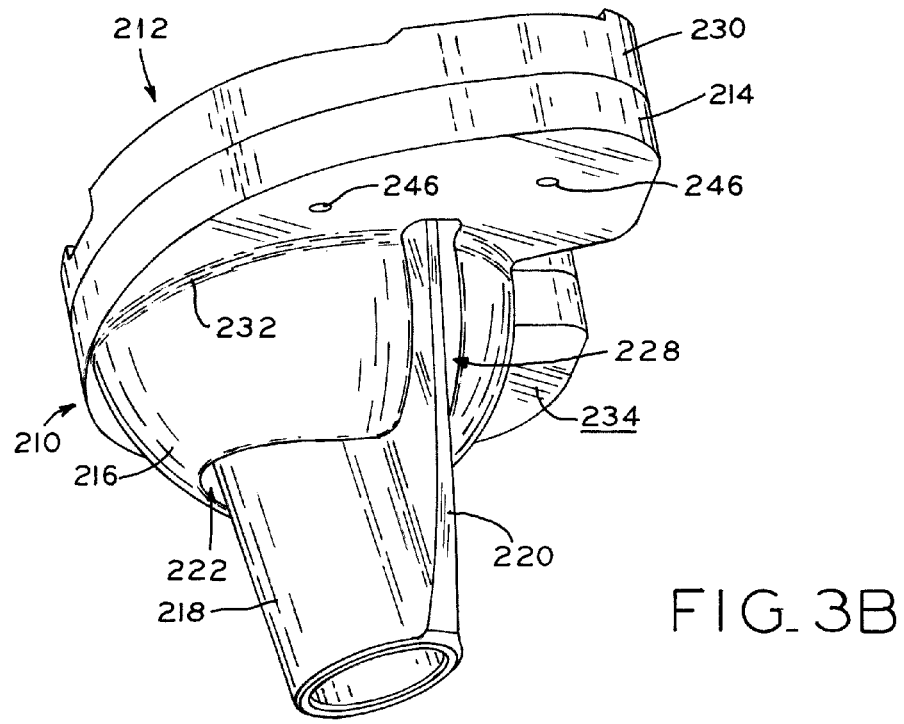
FIG_3B

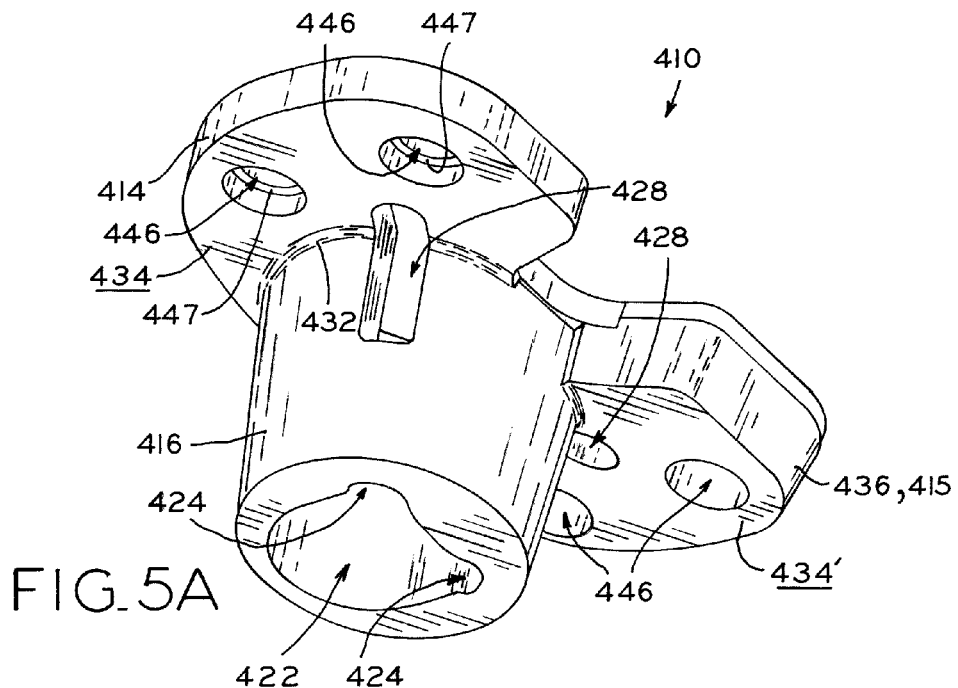
FIG_5A
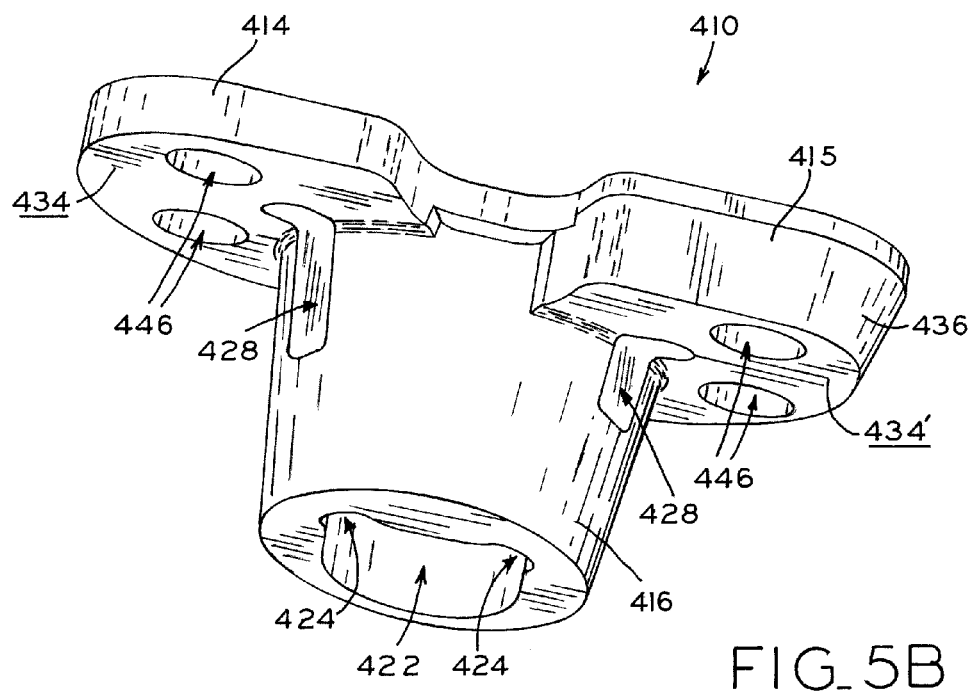
FIG_5B

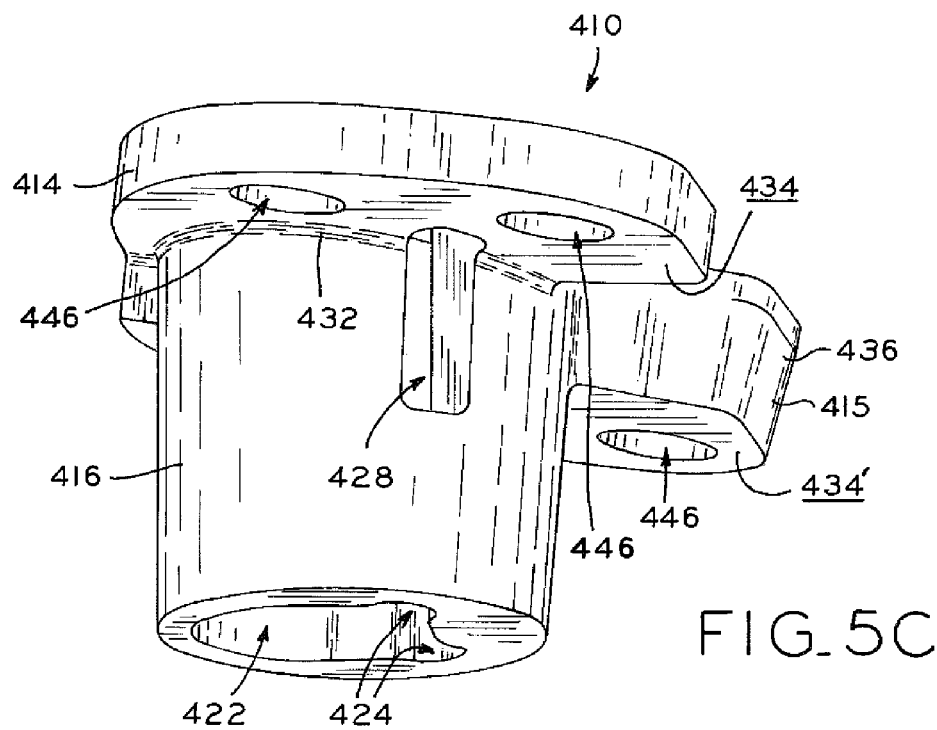
FIG_5C
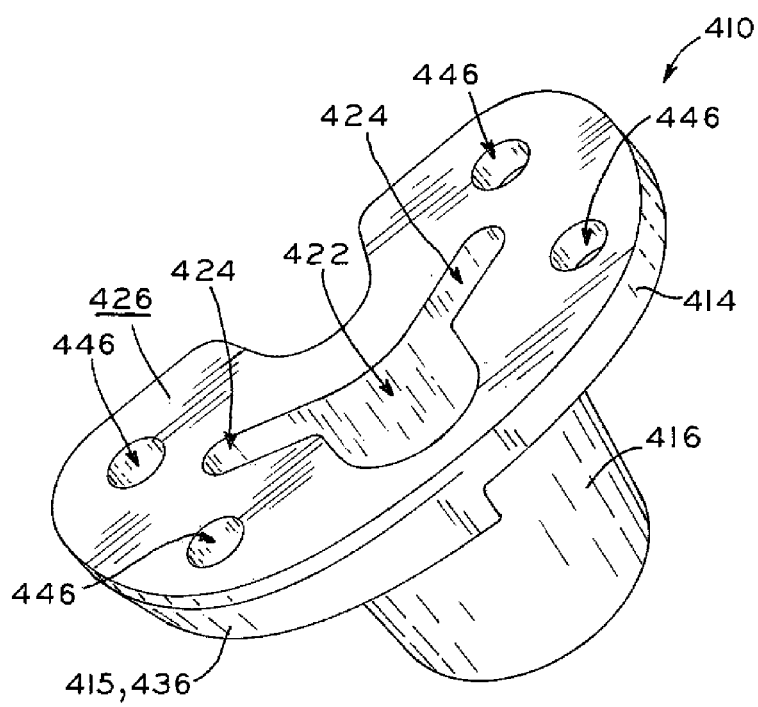
FIG_5D

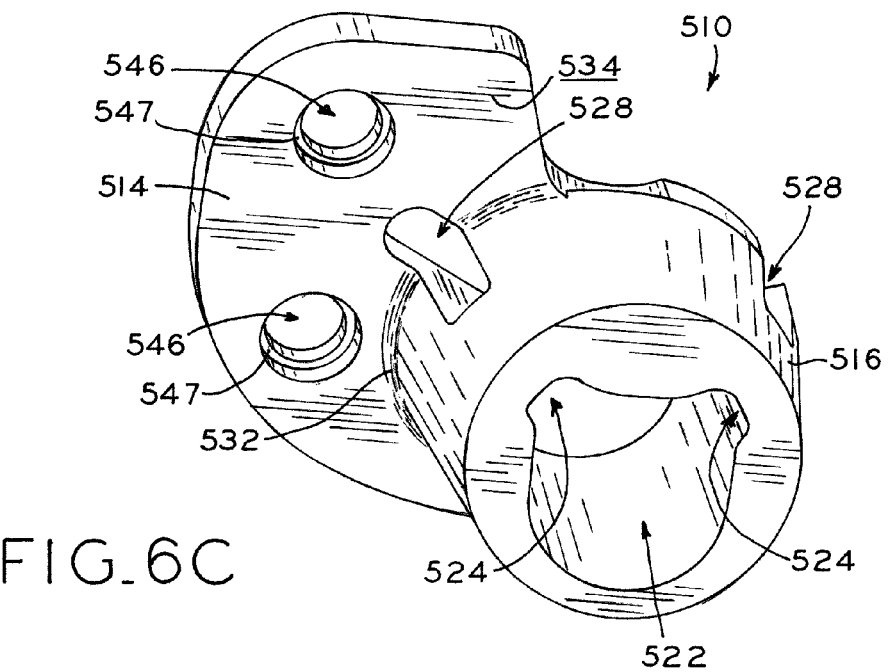
FIG_6C
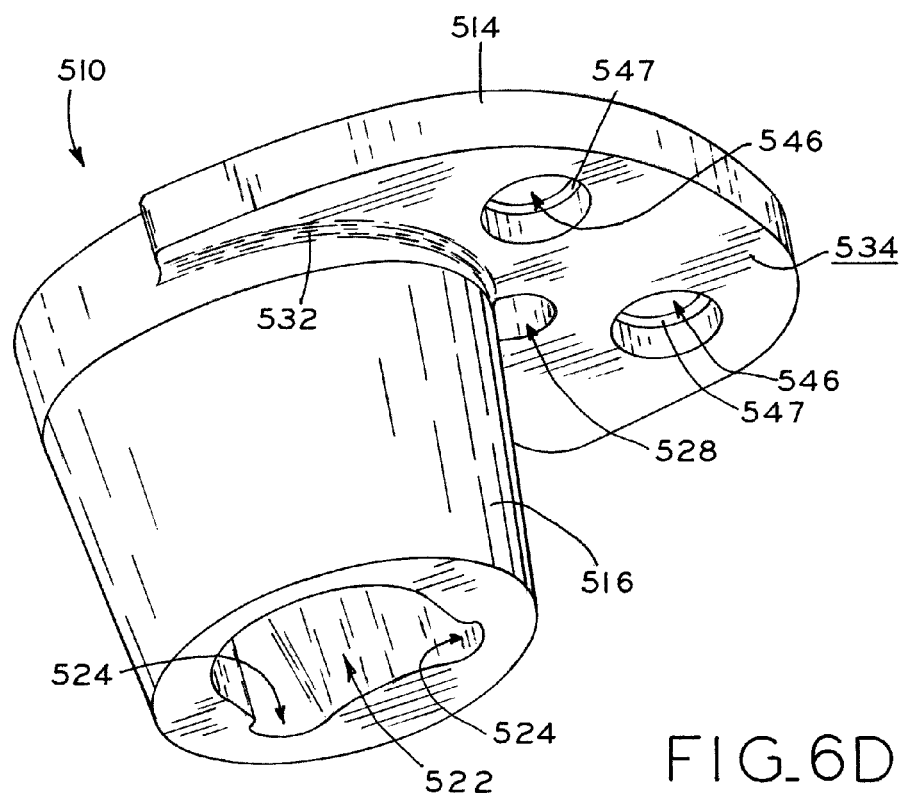
FIG_6D

STABILIZING PROSTHESIS SUPPORT STRUCTURE

CROSS-REFERENCE TO RELATED APPLICATION

This application claims the benefit under Title 35, U.S.C. §119(e) of U.S. Provisional Patent Application Ser. No. 61/488,549, filed May 20, 2011 and entitled STABILIZING PROSTHESIS SUPPORT STRUCTURE, the entire disclosure of which is hereby expressly incorporated herein by reference.

BACKGROUND

1. Technical Field

The present disclosure relates to orthopaedic prostheses, and more particularly, to stabilized tibial support structures for use with a knee prosthesis.

2. Description of the Related Art

Orthopaedic prostheses are commonly utilized to repair and/or replace damaged bone and tissue in the human body. For example, a knee prosthesis may be used to restore natural knee function by repairing damaged or diseased articular surfaces of the femur and/or tibia. Knee prostheses may include a femoral component implanted on the distal end of the femur, which articulates with a tibial component implanted on the proximal end of a tibia to replicate the function of a healthy natural knee.

One goal of knee replacement procedures is to reproduce or enhance the kinematics of the natural knee using the associated prosthetic components. More generally, such procedures seek to achieve kinematic characteristics that promote favorable patient outcomes such as minimized pain, proper joint function through a wide range of motion, and the longest possible prosthesis service life.

One aspect of establishing proper kinematics in a knee joint prosthesis is replication of the healthy natural "joint line" of the knee, i.e., the line spanning the medial and lateral points of contact between the femoral condyles and abutting tibial articular surfaces. To ensure that the natural joint line is preserved in the joint replacement procedure, the distal portion of the femur and the proximal portion of the tibia may each be resected by an amount corresponding to the thicknesses of the femoral and tibial components, respectively, such that the effective overall lengths of the femur and tibia remain unchanged after implantation of the prosthetic components.

However, in some cases the proximal tibia or distal femur may have severe degeneration, trauma, or other pathology which necessitates resection of more bone than can be compensated for by traditional femoral and tibial components. In such cases, augments may be used to effectively increase the thickness of the implanted component, thereby compensating for the additional thickness of the bone resection. Alternatively, a thicker prosthetic component can be employed instead of a component/augment combination.

In the proximal tibia, poor quality bone stock may also exist in the diaphyseal and/or metaphyseal region within the tibia. In such cases, a surgeon may opt for a second kind of augment, such as an augment having a generally cone-shaped outer profile corresponding to the generally cone-shaped bone defect typically encountered within the tibia. Exemplary tibial cone augments are disclosed in U.S. patent application Ser. No. 11/560,276, filed Nov. 15, 2006 and entitled PROSTHETIC IMPLANT SUPPORT STRUCTURE, and in U.S. patent application Ser. No. 12/886,297, filed Sep. 20, 2010 and entitled TIBIAL AUGMENTS FOR USE WITH KNEE JOINT PROSTHESES, METHOD OF IMPLANTING THE TIBIAL AUGMENT, AND ASSOCIATED TOOLS, both commonly assigned with the present application, the entire disclosures of which are hereby expressly incorporated by reference herein.

Where particularly acute degeneration of the proximal tibial bone stock has occurred, both a "cone" type augment and a "platform" type augment may be needed to i) replace resected bone stock within the tibia and ii) provide an elevated platform for a tibial baseplate component, respectively. In such cases, one or both of the augments may be cemented in place using bone cement, which adheres selected prosthetic knee components to one another and to the surrounding healthy bone stock. This bone cement may also be used join the pair of augments to one another, and to the tibial baseplate.

In some instances, such as where a knee prosthesis is implanted in a younger patient, a revision surgery may eventually become necessary to repair or replace damaged or worn out prosthesis components. Such revision surgery may require the removal and/or replacement of the tibial baseplate, which if cemented in place would typically be removed together with any augment components used in the previous surgery. Bone ingrowth into the material of the augment components may have occurred during the service life of the original prosthesis, possibly necessitating removal of additional healthy bone from the proximal tibia in order to fully dislodge the ingrown augment components.

SUMMARY

The present disclosure provides a tibial support structure that includes a platform portion and a medullary portion that are monolithically formed as a single piece. The medullary and platform portions of the augment component are adapted to accommodate and mechanically attach to a tibial baseplate, and are individually shaped and sized to replace damaged bone stock both within the medullar region of the tibia, as well at the tibial proximal surface. The monolithic formation of the tibial support structure provides a strong and stable foundation for a tibial baseplate and facilitates restoration of the anatomic joint line, even where substantial resections of the proximal tibia have been made. The tibial support structure may be made of a bone-ingrowth material which facilitates preservation and rebuilding of the proximal tibia after implantation, while also preserving the restored joint line by allowing revision surgeries to be performed without removal of the tibial support structure.

Advantageously, the tibial support structure may be implanted without the use of bone cement. The support structure/bone interface may be secured through the use of a porous bone ingrowth material on the outer surface of the support structure, such as highly porous tantalum material made in accordance with Trabecular Metal® technology available from Zimmer, Inc. of Warsaw, Ind. (Trabecular Metal® is a trademark of Zimmer, Inc.). The support structure/baseplate interface may be secured by mechanical attachment, such as through the use of fasteners. This cementless securement procedure facilitates future revision procedures by establishing a secure foundation for the tibial baseplate upon the proximal tibia, comprised of the support structure and ingrown bone, while also allowing the tibial baseplate to be mechanically disconnected from the support structure in the event of a revision surgery.

In one form thereof, the present disclosure provides a support structure for use in conjunction with a prosthesis component, the support structure comprising: a platform having a proximal surface and a distal surface defining a platform thickness therebetween, the proximal surface and the distal surface cooperating to define a platform outer periphery shaped to correspond with a periphery of a resected proximal tibia, the platform outer periphery defining a platform medial-lateral width and a platform anteroposterior length; and a medullary portion extending distally from the distal surface of the platform, the medullary portion monolithically formed with the platform and comprising: a medullary portion anteroposterior diameter less than the platform anteroposterior length; a medullary portion medial-lateral diameter less than the platform medial-lateral width; and a medullary portion height measured along a proximal/distal extent of the medullary portion.

In another form thereof, the present disclosure provides a support structure for use in conjunction with a prosthesis component, the support structure comprising: a platform having a proximal surface and a distal surface defining a platform thickness therebetween, the proximal surface and the distal surface cooperating to define a platform outer periphery shaped to correspond with a periphery of a resected proximal tibia, the periphery divided into a medial side and an opposing lateral side, the platform outer periphery defining a platform medial-lateral width and a platform anteroposterior length; and a medullary portion extending distally from the distal surface of the platform and from at least one of the medial side and the lateral side, the medullary portion monolithically formed with the platform and comprising: a medullary portion anteroposterior diameter less than the platform anteroposterior length; a medullary portion medial-lateral diameter; and a medullary portion height measured along a proximal/distal extent of the medullary portion.

In yet another form thereof, the present disclosure provides a support structure kit comprising: a first nominal size support structure comprising: a first platform having a proximal surface and a distal surface defining a first platform thickness therebetween, the proximal surface and the distal surface of the first platform cooperating to define a first platform outer periphery shaped to correspond with a periphery of a first resected proximal tibia, the first platform outer periphery divided into a medial side and an opposing lateral side, the platform outer periphery defining a first platform medial-lateral width and a first platform anteroposterior length; and a first medullary portion extending distally from the distal surface of the platform and from at least one of the medial side and the lateral side, the medullary portion monolithically formed with the platform and comprising: a first medullary portion anteroposterior diameter less than the first platform anteroposterior length; a first medullary portion medial-lateral diameter; and a first medullary portion height measured along a proximal/distal extent of the first medullary portion; and a second nominal size support structure larger than the first nominal size support structure, the second nominal size support structure comprising: a second platform having a proximal surface and a distal surface defining a second platform thickness therebetween, the proximal surface and the distal surface of the second platform cooperating to define a second platform outer periphery shaped to correspond with a periphery of a second resected proximal tibia, the second platform outer periphery divided into a medial side and an opposing lateral side, the platform outer periphery defining a second platform medial-lateral width and a second platform anteroposterior length; and a second medullary portion extending distally from the distal surface of the platform and from at least one of the medial side and the lateral side, the medullary portion monolithically formed with the platform and comprising: a second medullary portion anteroposterior diameter less than the second platform anteroposterior length; a second medullary portion medial-lateral diameter; and a second medullary portion height measured along a proximal/distal extent of the medullary portion; at least one of the first platform medial-lateral width, the first platform anteroposterior length, the first medullary portion anteroposterior diameter, the first medullary portion medial-lateral diameter, and the first medullary portion height smaller than a corresponding one of the second platform medial-lateral width, the second platform anteroposterior length, the second medullary portion anteroposterior diameter, the second medullary portion medial-lateral diameter, and the second medullary portion height.

The present disclosure provides a monolithic implant support structure which provides a stable implant mounting surface in a severely damaged or diseased bone. In the exemplary embodiments discussed below, the support structure provides a foundation for supporting a tibial baseplate that is resistant to subsidence while also facilitating replacement and/or augmentation of metaphyseal or diaphyseal bone within the tibia. The support structure may be made of a porous bone ingrowth material that provides a scaffold for bone ingrowth on multiple surfaces. These surfaces present large, three-dimensional areas of bone ingrowth material to the surrounding healthy bone for secure and stable long term fixation of the support structure to the proximal tibia. A tibial baseplate may be mechanically attached to the support structure, which facilitates later removal of the tibial baseplate during a revision surgery while preserving the prosthesis foundation provided by the support structure and ingrown bone.

A support structure in accordance with the present disclosure may be formed from a single piece of highly porous biomaterial. A highly porous biomaterial is useful as a bone substitute and as cell and tissue receptive material. A highly porous biomaterial may have a porosity as low as 55%, 65%, or 75% or as high as 80%, 85%, or 90%, or may have any porosity within any range defined by any of the foregoing values. An example of such a material is produced using Trabecular Metal® Technology generally available from Zimmer, Inc., of Warsaw, Ind. Trabecular Metal® is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 to Kaplan, the entire disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%, 85%, or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of the support structure to the patient's bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

The support structure may be formed from bone ingrowth material, such as porous tantalum as described above, which provides a scaffold for the ingrowth and interdigitation of bone with both the platform and the medullary portion of the support structure. As such ingrowth occurs over time, the support structure becomes integrally formed with the tibia to provide a stable, bone-like support foundation for a tibial baseplate. Advantageously, as noted below, this support foundation may remain in place even through a revision surgery to replace a tibial baseplate with a new tibial baseplate.

Generally, a small size support structure is adapted for a small size tibia and a relatively small medullary defect within such tibia, which is filled in by the medullary portion of the structure. A larger size support structure, on the other hand, is adapted for a larger tibia having a relatively large volume of defective bone within the tibia. However, it is contemplated that any size platform may be paired with any size medullary portion. In an exemplary embodiment, a family or kit of support structures may be provided with differing support structure size/geometry combinations. Each individual support structure may be suitable for one of a wide range of natural tibia sizes and bone defect geometries.

Support structures according to the invention may be used to restore the joint line of the natural knee where a large amount of the proximal tibia has been resected to remove correspondingly large amounts of diseased, damaged or otherwise defective bone stock. The combination of platforms into a single monolithic structure with medullary portions, ensures that this joint line is maintained over a long period of time by providing a large bone-contacting surface area. In addition, this monolithic combination presents many bone-contacting faces, each of which are oriented in a different direction with respect to the others to yield a "3-dimensional" or multi-faceted profile of bone-contacting faces. This 3-dimensional profile facilitates multidirectional stabilization of the support structure, and of the tibial baseplate mounted thereto, thereby minimizing or eliminating subsidence, anteroposterior movement and medial-lateral movement of the tibial prosthesis in vivo. Moreover, it has been found that the stability provided by a monolithic support structure made in accordance with the present disclosure provides greater stability than would otherwise be provided by a separate tibial cone-shaped implant and a plate-shaped tibial augment implant, whether used in combination or alone.

Advantageously, a support structure made in accordance with the present disclosure does not require the use of cement for fixation to a bone. This lack of cement facilitates bone ingrowth by allowing bone to interdigitate more deeply with the porous bone contacting surfaces of the platform. This deep bone ingrowth provides stronger and more secure fixation than could be expected from adhesion between bone cement and bone. Thus, a support structure in accordance with the present disclosure provides a bone replacement and restoration mechanism which gives rise to a stable, bone-like support structure for tibial baseplate components and other associated knee prosthesis components.

Also advantageously, the tibial baseplates are removable from their support structures in a revision surgery, even if substantial bone ingrowth has occurred between the tibia and support structures. Because no cement is required, as discussed above, cemented fixation between a tibial baseplate and a support structure in accordance with the present disclosure is not required. Rather, mechanical fixation may be used, such as with a fastener and a nut. If a revision surgery is required, such mechanical fixation can be reversed by removing fastener from the nut, thereby freeing the tibial baseplate from the support structure. The support structure can be left behind, and may therefore remain thoroughly interdigitated with ingrown bone. This remaining support structure obviates the need for removal of any further bone stock during a revision surgery, and provides a reusable, stable and strong support platform for a new tibial baseplate and/or other knee prosthesis components.

Further, the strength of fixation between a support structure in accordance with the present disclosure and the adjacent bone is unexpectedly stronger than other designs adapted for use without bone cement. The monolithic, integral nature of the support structure results in a stronger implant as compared to two separate implants separately affixed to the bone. Thus, the overall area of bone ingrowth for the support structures is substantially larger than any other similarly sized individual tibial augment structure.

BRIEF DESCRIPTION OF THE DRAWINGS

The above mentioned and other features and advantages of this disclosure, and the manner of attaining them, will become more apparent and the invention itself will be better understood by reference to the following description of embodiments of the invention taken in conjunction with the accompanying drawings, wherein:

FIG. 1A is a perspective view of a relatively small-sized tibial baseplate with a baseplate support structure made in accordance with the present disclosure attached thereto;

FIG. 1B is another perspective view of the support structure shown in FIG. 1A;

FIG. 1F is a side, elevation view of the support structure shown in FIG. 1B;

FIG. 1G is a top, plan view of the support structure shown in FIG. 1B;

FIG. 2C is a side, elevation view of the tibial baseplate and support structure shown in FIG. 2A;

FIG. 2D is an anterior, elevation view of the tibial baseplate and support structure shown in FIG. 2A;

FIG. 2E is an anterior, elevation view of the tibial baseplate support structure shown in FIG. 2A;

FIG. 3A is a perspective view of a tibial baseplate with a tibial baseplate support structure made in accordance with the present disclosure attached thereto, in which the support structure has a hemispherical medullary portion;

FIG. 3B is another perspective view of the tibial baseplate and support structure shown in FIG. 3A;

FIG. 5A is a perspective view of a tibial baseplate support structure having a stepped platform portion in accordance with the present disclosure;

FIG. 5B is another perspective view of the support structure shown in FIG. 5A;

FIG. 5C is another perspective view of the support structure shown in FIG. 5A;

FIG. 5D is another perspective view of the support structure shown in FIG. 5A;

FIG. 6C is another perspective view of the support structure shown in FIG. 6A;

FIG. 6D is another perspective view of the support structure shown in FIG. 6A;

Corresponding reference characters indicate corresponding parts throughout the several views. The exemplifications set out herein illustrate exemplary embodiments of the present invention, and such exemplifications are not to be construed as limiting the scope of the invention in any manner.

DETAILED DESCRIPTION

Figure 1C:
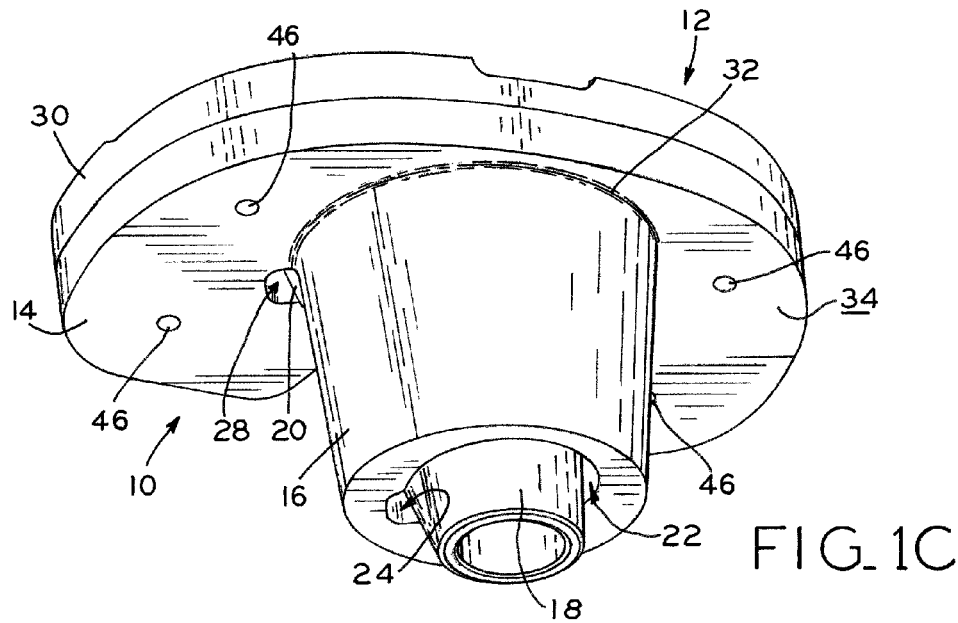
FIG. 1C is another perspective view of the tibial baseplate and support structure shown in FIG. 1A.

The present disclosure provides a monolithic implant support structure which provides a stable implant mounting surface in a severely damaged or diseased bone. In the exemplary embodiments discussed below, the support structure provides a foundation for supporting a tibial baseplate that is resistant to subsidence while also facilitating replacement and/or augmentation of metaphyseal or diaphyseal bone within the tibia. The support structure may be made of a porous bone ingrowth material that provides a scaffold for bone ingrowth on multiple surfaces. These surfaces present large, three-dimensional areas of bone ingrowth material to the surrounding healthy bone for secure and stable long term fixation of the support structure to the proximal tibia. A tibial baseplate may be mechanically attached to the support structure, which facilitates later removal of the tibial baseplate during a revision surgery while preserving the prosthesis foundation provided by the support structure and ingrown bone.

A support structure in accordance with the present disclosure may be formed from a single piece of highly porous biomaterial. A highly porous biomaterial is useful as a bone substitute and as cell and tissue receptive material. A highly porous biomaterial may have a porosity as low as 55%, 65%, or 75% or as high as 80%, 85%, or 90%, or may have any porosity within any range defined by any of the foregoing values. An example of such a material is produced using Trabecular Metal® Technology generally available from Zimmer, Inc., of Warsaw, Ind. Trabecular Metal® is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 to Kaplan, the entire disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%, 85%, or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of the support structure to the patient's bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

Various configurations and sizes for a support structure are contemplated in accordance with the present disclosure. Exemplary configurations are provided in the description below and associated drawings. For example, FIGS. 1A-1G illustrate a monolithic (or "monoblock") support structure for a relatively small size tibial baseplate and a correspondingly small medullary defect. In FIGS. 2A-2H, a second monolithic support structure similar to the support shown in FIGS. 1A-1G is illustrated, but is adapted for a larger size tibial baseplate and a correspondingly larger medullary defect. FIGS. 3A-3H illustrate yet another monolithic support structure with a medullary portion having an alternative geometrical configuration, namely, a hemispherical configuration.

Turning now to FIG. 1A, a nominally small-sized baseplate support structure 10 is shown mated to a correspondingly small nominal size tibial baseplate 12. Support structure 10 includes proximal platform 14, which mechanically attaches to the distal surface of tibial baseplate 12 (as described below) and has an outer periphery substantially matching the outer periphery of baseplate 12, which in turn has a periphery shaped to correspond with a proximal resected surface $T_S$ of an anatomic tibia T (FIG. 1H). Medullary portion 16 extends distally from distal surface 34 of platform 14, and is integrally, monolithically formed with platform 14 such that support structure 10 is formed from a single, monolithic piece of material.

In the illustrated embodiments discussed below, support structure 10 is formed from bone ingrowth material, such as porous tantalum as described above, which provides a scaffold for the ingrowth and interdigitation of bone with both platform 14 and medullary portion 16 of support structure 10. As such ingrowth occurs over time, support structure 10 becomes integrally formed with the tibia to provide a stable, bone-like support foundation for tibial baseplate 12. Advantageously, as noted below, this support foundation may remain in place even through a revision surgery to replace tibial baseplate 12 with a new tibial baseplate.

Medullary portion 16 is generally conically shaped, as described in detail below, and includes opening 22 through which baseplate keel 18 may pass. In the illustrative embodiment, medullary portion 16 has a substantially closed peripheral profile, such that keel 18 is surrounded by opening 22. As most clearly shown in FIG. 1B, baseplate keel 18 includes a pair of fins 20 extending between the distal end of keel 18 and the distal surface of the tibial baseplate 12. To accommodate fins 20, opening 22 includes flared cutouts 24 extending therethrough. Cutouts 24 interrupt the otherwise conical or cylindrical shape of opening 22, and selectively expand the periphery of opening 22 along the longitudinal extent of medullary portion 16 to provide a space sized to fit fins 20 with clearance. As cutouts 24 extend toward the proximal end of opening 22 (at proximal surface 26, as shown in FIG. 1G), cutouts 24 flare outwardly to accommodate the corresponding outward flare of fins 20 as they extend toward their junction with platform portion 30 of tibial baseplate 12.

Figure 1D:
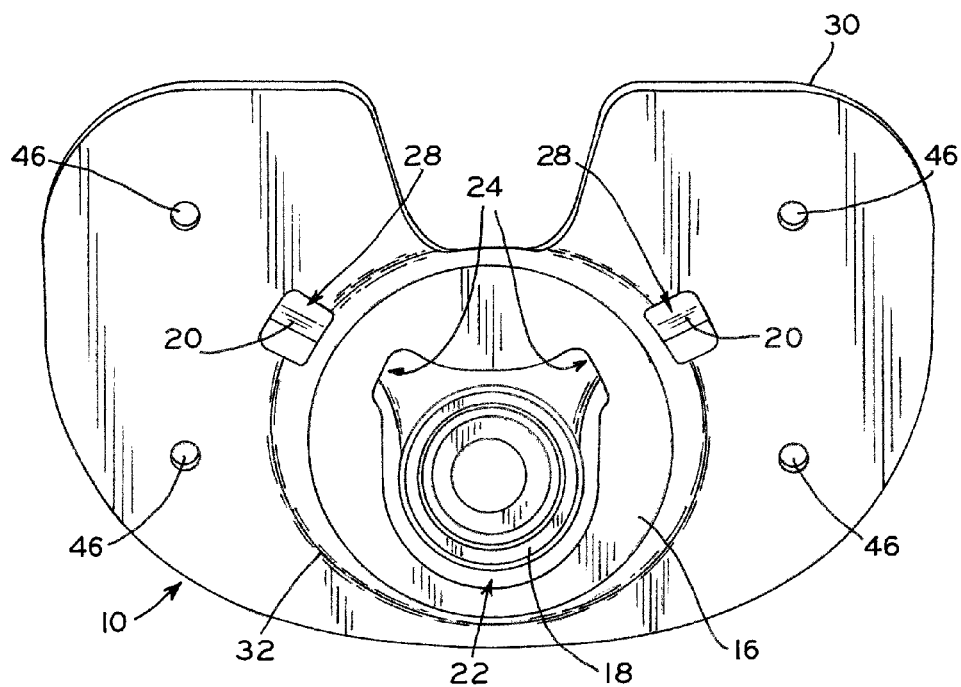
FIG. 1D is a bottom, plan view of the tibial baseplate and support structure shown in FIG. 1A.

In the illustrated embodiment of FIGS. 1C and 1D, baseplate fins 20 do not protrude outwardly beyond the outer periphery of medullary portion 16. In order to maintain a desired minimum material thickness throughout support structure 10, however, fin windows 28 are formed in the material of support structure 10. In an exemplary embodiment, the minimum material thickness in support structure is at least 1 mm. Fin windows 28 span an area from a distal window end, at which fins 20 are sufficiently proximate to medullary portion 16 to prevent the desired minimum material thickness from being achieved, to a proximal window end at distal surface 34 of platform portion 14. Thus, fin windows 28 span junction 32 formed between medullary portion 16 and platform 14 of support structure 10.

The size of the interruptions in junction 32 caused by fin windows 28 is minimized in order to maximize the strength of junction 32 between medullary portion 16 and platform 14. At the same time, the size of windows 28 is made sufficiently large to maintain at least a minimum desired clearance between keel 18 and the interior surface defined by opening 22 of medullary portion 16. Junction 32 is also radiused to prevent stress concentrations within the material of support structure 10 during in vivo prosthesis use.

As best seen in FIGS. 1C and 1D, clearance is provided between the peripheral wall of opening 22 formed through medullary portion 16 of support structure 10, and the outer peripheral wall of tibial baseplate keel 18. This clearance ensures a smooth passage of keel 18 through opening 22 upon assembly of baseplate 12 to support structure 10, and further ensures that the orientation of tibial baseplate 12 with respect to support structure 10 after such assembly is dictated solely by the interface between platform 14 of support structure 10 and platform portion 30 of tibial baseplate 12. The clearance between keel 18 and medullary portion 16 may be the same as clearance 148 between keel 118 and medullary portion 116 of larger-sized support structure 110, as illustrated in FIG. 2H and described below.

Figure 1E:
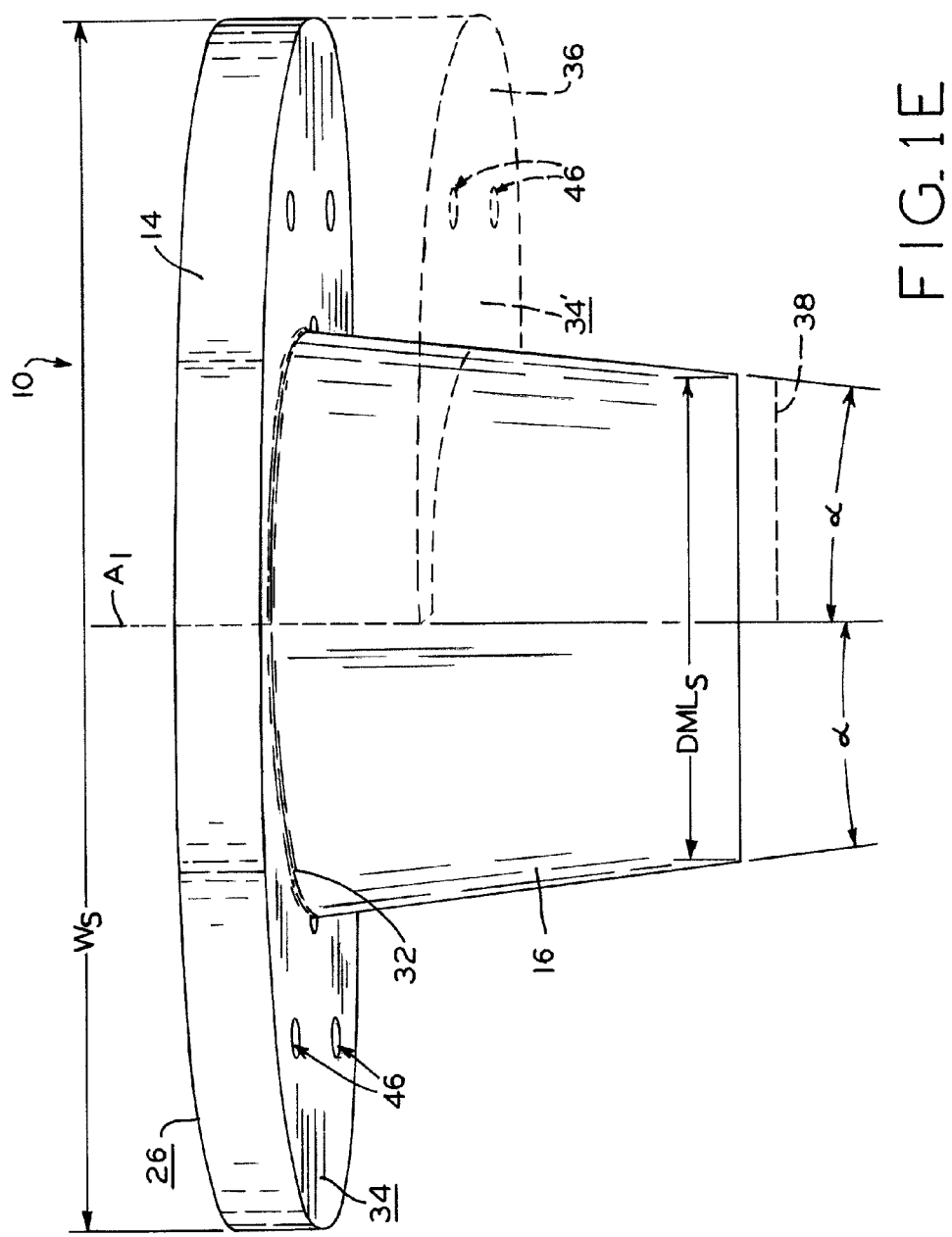
FIG. 1E is an anterior, elevation view of the support structure shown in FIG. 1B.
Figure 1H:
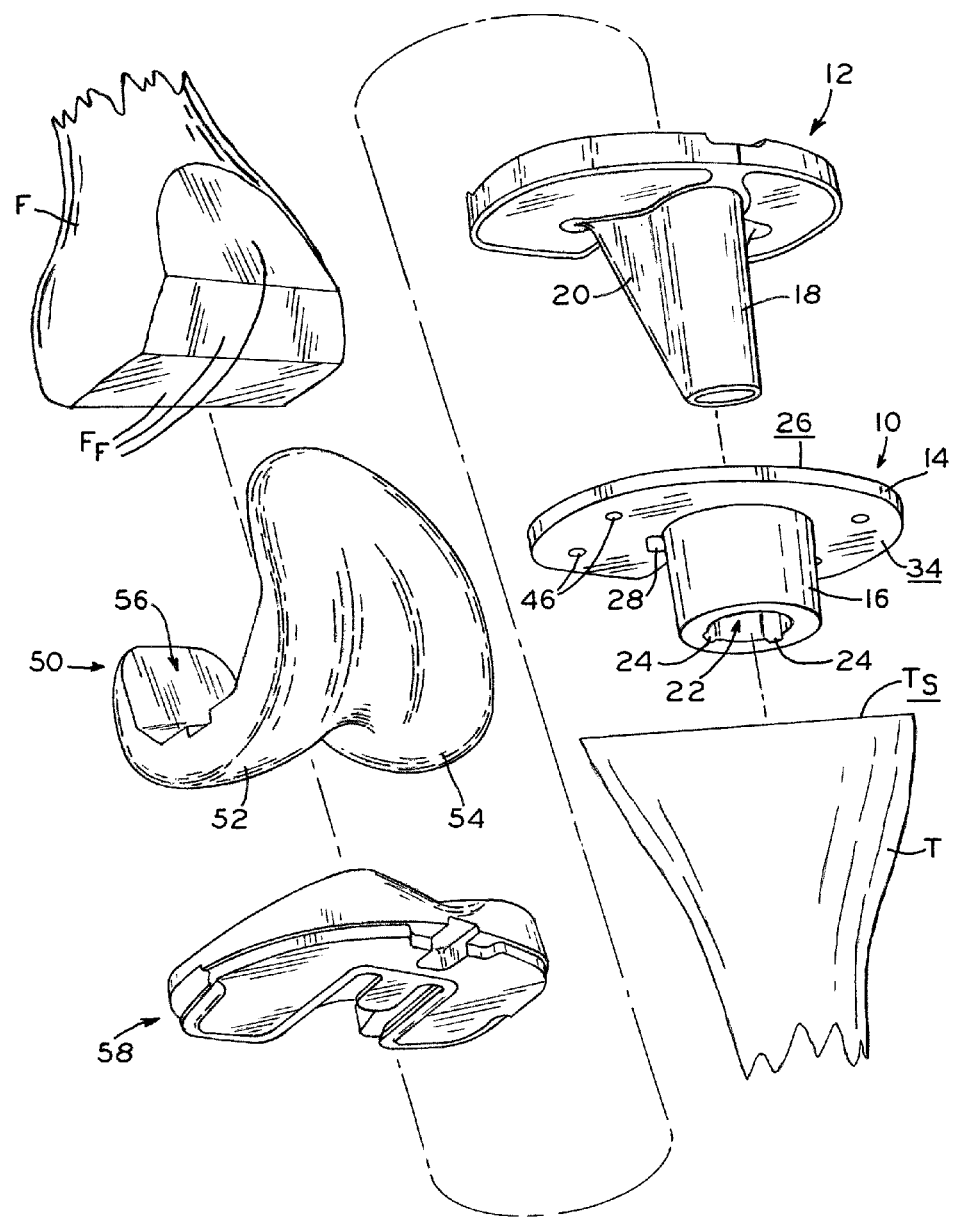
FIG. 1H is an exploded, perspective view of knee prosthesis components made in accordance with the present disclosure and suitable for use in a total knee replacement surgery.

In the illustrative embodiment of FIGS. 1A-1G, medullary portion 16 of support structure 10 has a truncated, generally conical outer surface. As shown in FIGS. 1E and 1F, the truncated cone defined by medullary portion 16 defines a central axis $A_1$. When viewed from different aspects, this truncated cone defines varying degrees of taper with respect to axis $A_1$. Referring to FIG. 1E, for example, the tapers defined by the medial and lateral boundaries of medullary portion 16 (i.e., the taper when viewed from an anterior or posterior perspective) defines taper angle α with respect to axis $A_1$. On the other hand, referring to FIG. 1F, the posterior boundary of medullary portion 16 defines taper angle β, and no taper is defined by the anterior boundary of medullary portion 16. Thus, while the present disclosure refers generically to truncated "cone shaped" augments and portions of augments, it is contemplated that such cone shapes need not be strictly conical, but can have varying cross-sectional geometries such as oval, elliptical, or any other non-circular cross-section.

It is contemplated that the taper angles defined by support structure 10 may have a variety of nominal values or combinations of nominal values. For example, the medial and lateral taper angles α (FIG. 1E) may be equal (as shown) or different, and may define any taper angle. In one exemplary embodiment, angle α is as little as 4 degrees or 9.5 degrees and as large as 12 degrees or 15 degrees, or may be any value within any range defined by any of the foregoing values. Posterior taper angle β may be as little as 10 degrees or 12 degrees, or as large as 17 degrees or 19 degrees, or may be any value within any range defined by any of the foregoing values. In this exemplary embodiment, no anterior taper angle is defined by medullary portion 16, i.e., the anterior edge of medullary portion 16 is substantially parallel to axis $A_1$ as viewed from the sagittal perspective of FIG. 1F. However an anterior taper angle may be provided as desired or required for a particular application, such that the anterior edge of medullary portion 16 converges toward axis $A_1$ along a proximal-to-distal direction. Additional discussion of exemplary taper angles for medullary portion 16, in the context of a separately formed conically-shaped augment, appears in U.S. patent application Ser. No. 12/886,297, incorporated by reference above.

As best shown in FIGS. 1C and 1E, distal surface 34 of platform 14 defines a substantially flat, planar surface adapted to mate with a similarly planar resected surface of a proximal tibia. However, as illustrated in FIG. 1E, it is contemplated that distal surface 34 may be "stepped" such that one of the medial and lateral side of support structure 10 is thicker than the other side. This thicker side 36 defines stepped distal surface 34', which is positioned to rest upon a portion of the tibia which has been more deeply resected than the other, adjacent portion of the resected tibia. Such a "stepped" configuration may prevent unnecessary removal of healthy bone in an asymmetric defect. More particularly, a surgeon may avoid resection of healthy bone stock on one side of the tibial plateau where no augmentation is required, while resecting damaged bone from the other side where more severe trauma and/or degradation has occurred.

Another embodiment including a stepped configuration of the distal surface of the augment platform is illustrated in FIGS. 5A-5F. Support structure 410 is similar to support structure 10 described above, and reference numbers in FIGS. 5A-5F refer to analogous structures described above with respect to support structures 10. However, platform portion 414 includes a thicker side 436 on the opposite side of support structure 410 as compared to thicker side 36 of support structure 10. Distal surface 434' is offset distally from distal surface 434 in a similar fashion as described above. At the periphery of platform 414, however, thicker side 436 includes tapered portion 415, similar to tapered portion 115 described below with respect to larger-sized support structure 110 (FIGS. 2A-2H). Holes 446 are also modified in support structure 410 to include shoulders 447 therein. Shoulders 447 are sized and adapted to engage shoulder 43 of nut 42 (FIG. 1A) to axially capture nut 42 within holes 446.

Another embodiment including an asymmetric platform configuration is illustrated in FIGS. 6A-6G. Support structure 510 is similar to support structure 10 described above, and reference numbers in FIGS. 6A-6G refer to analogous structures described above with respect to support structures 10. However, only one side of platform portion 514 is provided, such that support structure is only designed to replace either medial or lateral defects in the proximal tibia while leaving the other side un-augmented. In the illustrated embodiment, support structure 510 can be used to replace defects in the lateral tibial plateau when used in a left knee, or in the medial tibial plateau when used in a right knee. It is also contemplated that a similar, substantially mirror-image support structure may be provided for augmentation of bone resected to remove left-medial and right-lateral defects. In another alternative, the overall shape of the augment may be asymmetric, such that individual asymmetric component geometries may be provided for each of right-lateral, right-medial, left-lateral and left-medial defects. Like holes 446 of support structure 410, holes 546 include shoulders 547.

In addition to the various geometrical arrangements of platforms 14, 414, 514 described above, it is contemplated that medullary portion 16 may have an extended axial length on one side, as represented by extended axial portion 38 of medullary portion 16 in FIG. 1E. Similar to thicker side 36, this additional axial length on one side allows a surgeon to correct an asymmetric medullary defect without removal of healthy bone on a side of the bone lacking such defects.

Referring back to FIG. 1A, support structure 10 mounts to tibial baseplate 12 via externally threaded fastener 40 and a corresponding internally threaded nut 42. Platform portion 30 of tibial baseplate 12 includes a plurality of countersunk holes 44 sized to receive the head of fastener 40. Upon assembly, fastener 40 passes through holes 44 and into correspondingly formed holes 46 formed in platform 14 of support structure 10 (FIG. 1B), which are aligned with holes 44 when support structure 10 and baseplate 12 are coupled to one another. Nut 42 is received within holes 46, such that fastener 40 may be threadably engaged with nut 42. Shoulder 43 axially fixes nut 42 with respect to distal surface 34 of support structure 10, so when fastener 40 is tightened, fastener 40 and nut 42 cooperate to mechanically fasten support structure 10 to tibial baseplate 12. Fasteners 40, nut 42 and tibial baseplate 12 may be made of a biocompatible material, such as titanium or cobalt chrome molybdenum. Such mechanical fixation facilitates revision surgeries by allowing tibial baseplate 12 to be removed from support structure 10 by disengaging fasteners 40 from respective nuts 42. Thus, even when support structure 10 has become embedded within the tibia over time via bone ingrowth into support structure 10, tibial baseplate remains removable without removal of support structure 10 or the surrounding bone.

FIG. 1H illustrates the use of support structure 10 and tibial baseplate 12 in conjunction with other prosthesis components used in a total knee replacement (TKR) surgical procedure. In particular, femoral component 50 may be provided for implantation upon femur F, in order to replace the articular surfaces of the natural femoral condyles with prosthetic condyles 52, 54. Femur F may be prepared to receive femoral component 50 by resection of the femoral condyles to create femoral facets $F_F$, which are positioned and configured to abut the corresponding facets of bone-contacting surface 56 of femoral component 50.

Tibial bearing component 58 may be fitted to tibial baseplate 12 in order to provide a low-friction articular interface with condyles 52, 54 of femoral component 52. In one exemplary embodiment, tibial bearing component 58 cooperates with tibial baseplate 12 to form a "fixed bearing" design in which tibial bearing component 58 is immovably affixed to tibial baseplate 12 upon implantation. In another exemplary embodiment, tibial bearing component 58 is a "mobile bearing" design in which tibial bearing component is slidably and/or rotatably movable with respect to tibial baseplate 12 during knee articulation.

Tibial baseplate 12 and support structure 10 are affixed to tibia T upon prosthesis implantation. In one embodiment, the anatomic articular surfaces of tibia T are resected to create a substantially planar resected surface $T_S$, which is configured to abut the substantially planar distal surface 34 of support structure 10. A resected, generally conical cavity is also formed in tibia T to correspond with medullary portion 16 of support structure 10. An exemplary apparatus and method for forming medullary portion 16 is disclosed in U.S. provisional patent application Ser. No. 61/522,872 filed Aug. 12, 2011 and entitled PROSTHESIS RESECTION GUIDE, the entire disclosure of which is hereby expressly incorporated herein by reference.

Figure 2A:
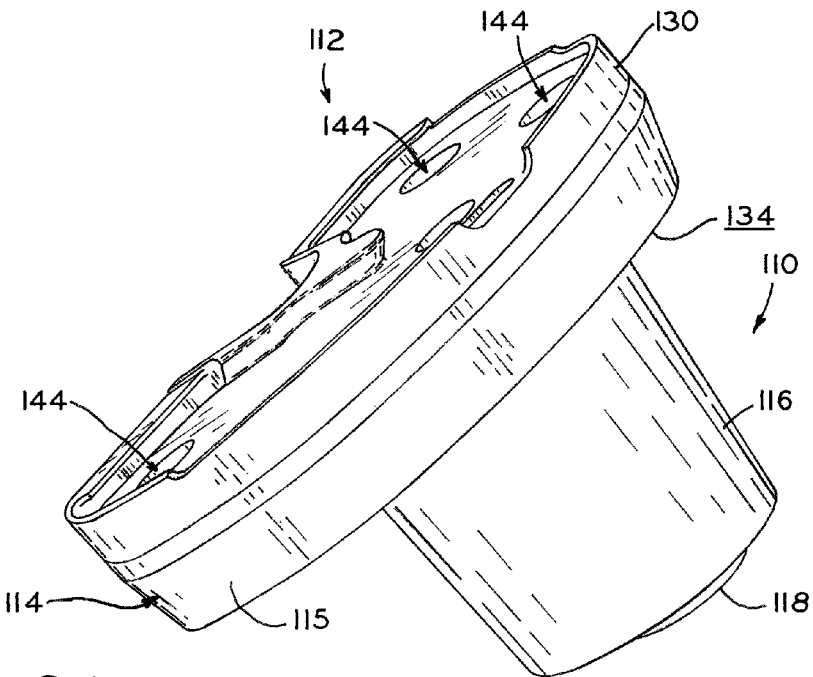
FIG. 2A is a perspective view of a relatively large-sized tibial baseplate with a tibial baseplate support structure made in accordance with the present disclosure attached thereto.
Figure 2B:
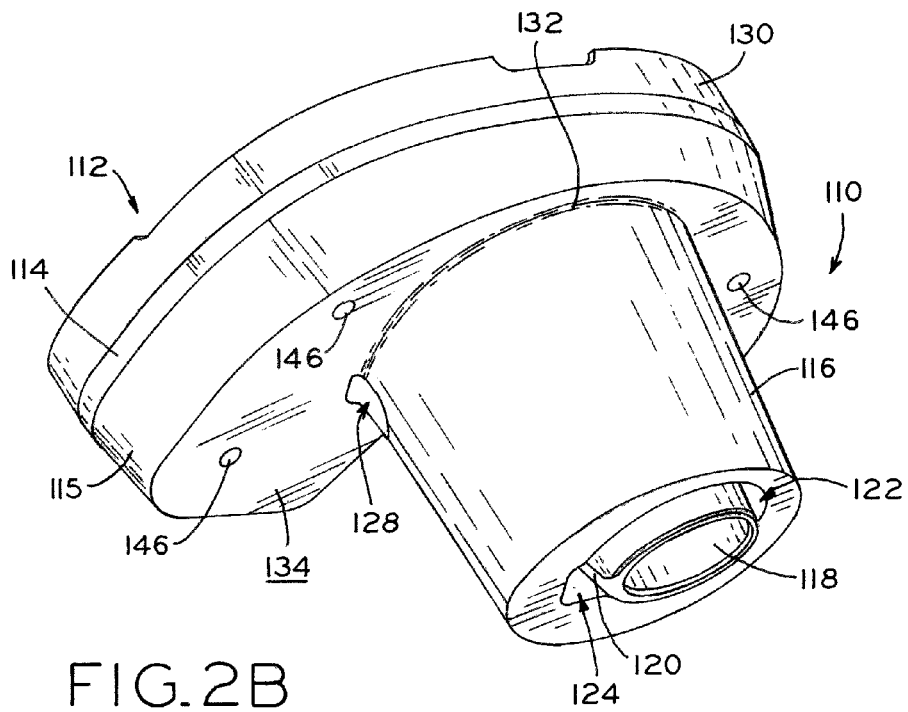
FIG. 2B is another perspective view of the tibial baseplate and support structure shown in FIG. 2A.

Turning now to FIGS. 2A and 2B, a relatively larger nominal size of support structure 110 is shown mated to a corresponding larger nominal size of tibial baseplate 112. Support structure 110 and baseplate 112 are generally similar to the small nominal size support structure 10 and correspondingly small tibial baseplate 12, discussed in detail above, but are larger in dimension to accommodate larger natural anatomies. Reference numbers in FIGS. 2A-2H refer to analogous structures described above with respect to support structures 10.

Referring to a comparison of FIGS. 1E and 2E, for example, large size support structure 110 defines an overall width $W_L$ of platform 114 that is larger than the corresponding width $W_S$ of platform 14. The distal end of medullary portion 116 defines a medial-lateral diameter $DML_L$ which is also correspondingly larger than medial-lateral diameter $DML_S$ of the relatively smaller medullary portion 16 of support structure 10. It should be appreciated that the term "diameter" as used herein does not necessarily imply a round cross-section, but may also refer to a dimension across a non-round cross section. For example, a diameter may be the major or minor axes of an ellipse, oval or other oblong shape.

Figure 2F:
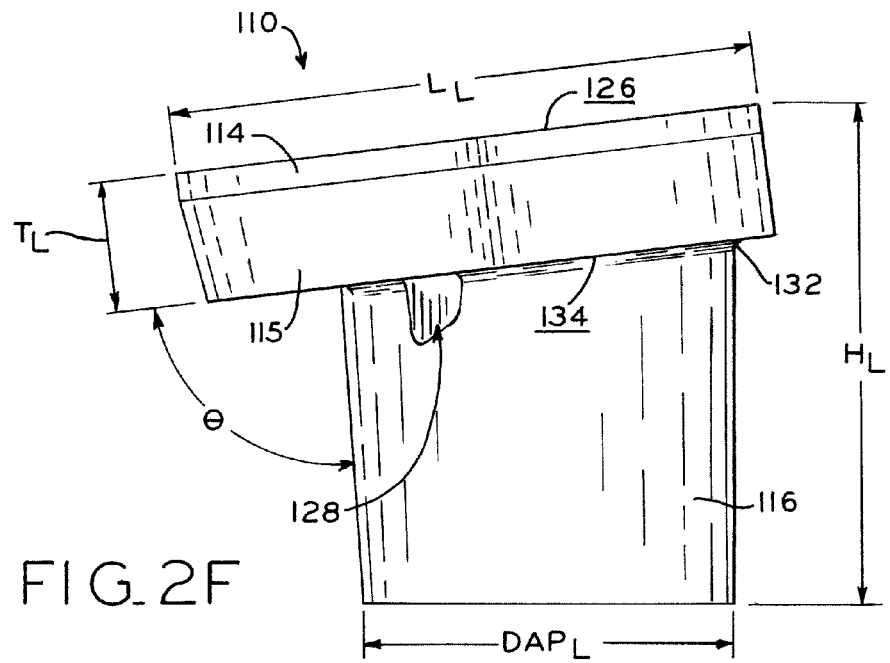
FIG. 2F is a side, elevation view of the support structure shown in FIG. 2E.
Figure 2G:
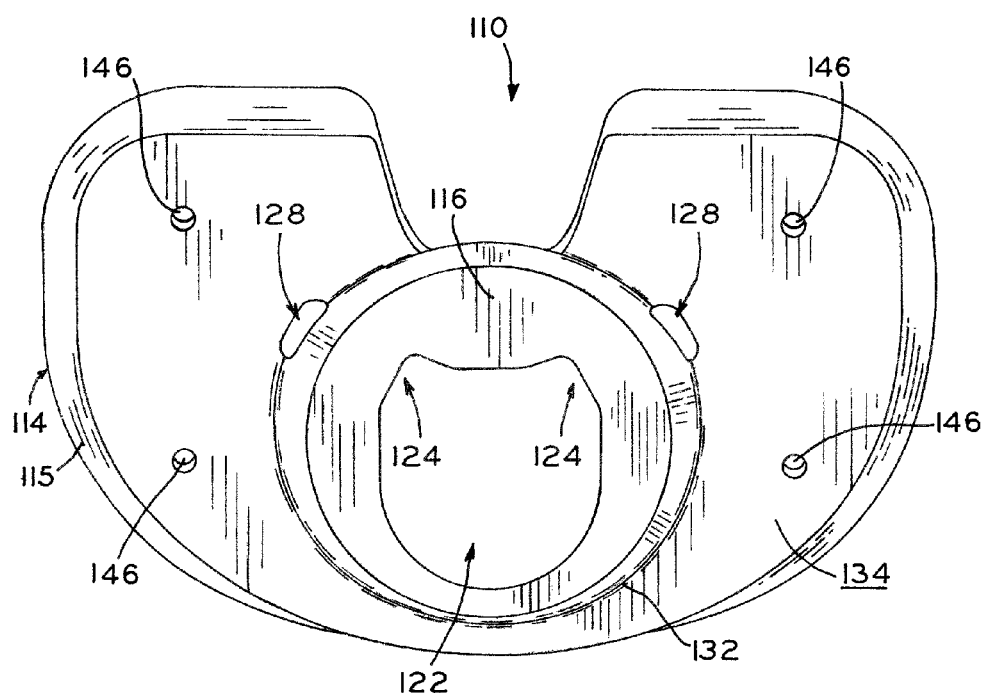
FIG. 2G is a bottom, plan view of the support structure shown in FIG. 2E.
Figure 2H:
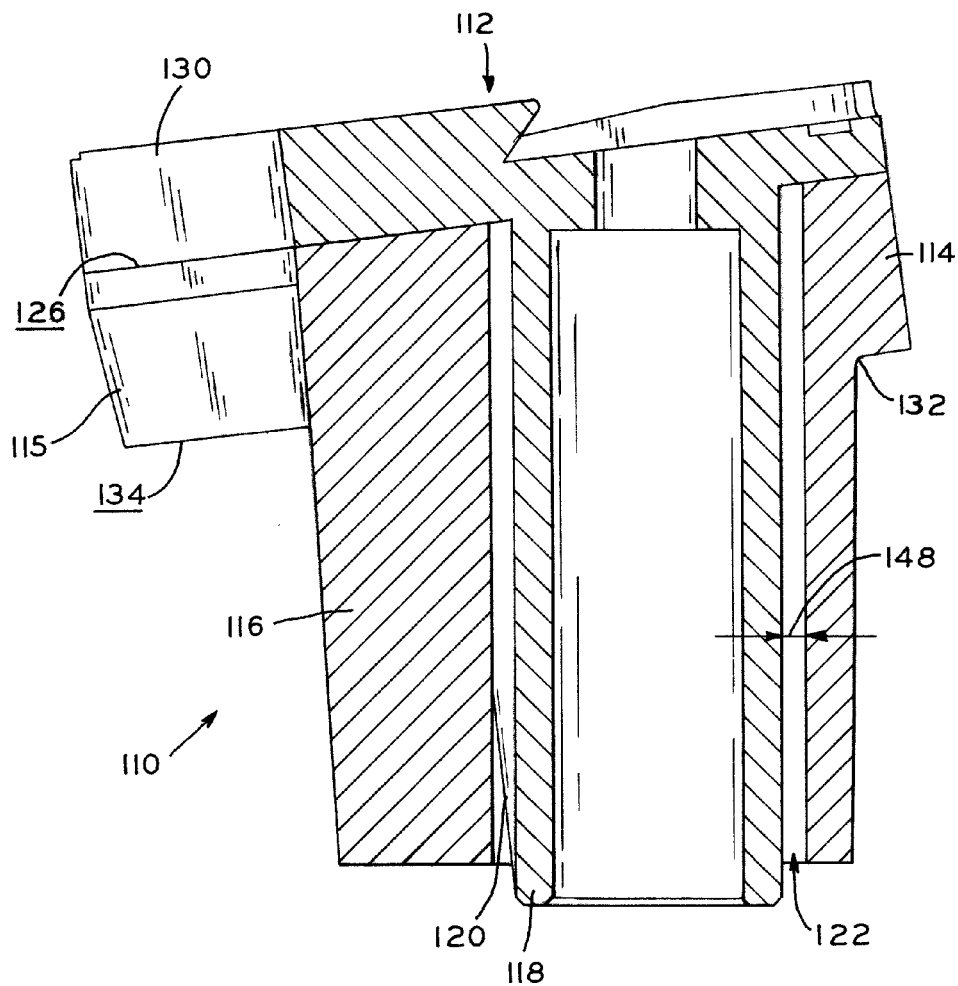
FIG. 2H is a side, elevation, section view of the tibial component and support structure shown in FIG. 2C.

Turning to a comparison of FIGS. 1F and 2F, large size support structure 110 defines an overall height $H_L$, and anteroposterior length $L_L$ of platform 114, and an anteroposterior diameter $DAP_L$ of medullary portion 116 that are larger than the corresponding height $H_S$, length $L_S$, and medullary portion diameter $DAP_S$ of the relatively smaller support structure 10. Smaller and larger sized support structures 10, 110 each define angle β between platforms 14, 114 and the posterior portion of medullary portions 16, 116, respectively. It is contemplated that angles α, β and θ may be different among different support structure configurations.

Moreover, small size support structure 10 is generally adapted for a small size tibia and a relatively small medullary defect within the tibia, which is filled in by medullary portion 16 as described in detail below. Larger size support structure 110, on the other hand, is adapted for a larger tibia having a relatively large volume of defective bone within the tibia. However, it is contemplated that any size platform may be paired with any size medullary portion. In an exemplary embodiment, a family or kit of support structures may be provided with differing support structure size/geometry combinations. Each individual support structure may be suitable for one of a wide range of natural tibia sizes and bone defect geometries.

In an exemplary embodiment, support structure dimensions may be any of the following values, or may be any value within any range defined by the following values: support structure height $H_S$ may be as little as 2 mm, 5 mm or 10 mm, while height $H_L$ may be as much as 60 mm, 80 mm or 100 mm; support structure length $L_S$ may be as little as 40 mm, 50 mm or 60 mm, while length $L_L$ may be as much as 90 mm, 110 mm or 130 mm; anteroposterior diameter $DAP_S$ may be as little as 10 mm, 30 mm or 50 mm, while anteroposterior diameter $DAP_L$ may be as much as 60 mm, 80 mm or 100 mm; support structure width $W_S$ may be as little as 50 mm, 60 mm or 70 mm, while width $W_L$ may be as much as 90 mm, 110 mm or 130 mm; medial-lateral diameter $DML_S$ may be as little as 10 mm, 30 mm or 50 mm, while medial-lateral diameter $DML_L$ may be as much as 90 mm 110 mm or 130 mm; support structure thickness $T_s$ may be as little as 1 mm, 3 mm or 5 mm, while thickness $T_L$ may be as much as 20 mm, 25 mm or 30 mm. An overall height of medullary portions 16, 116 may be determined by subtracting thickness $T_S$, $T_L$ from overall structure height $H_S$, $H_L$ respectively.

Larger size support structure 110, in addition to having larger nominal dimensions as detailed above, may also have certain unique geometrical characteristics. For example, referring to FIG. 2A, platform 114 includes tapered portion 115, which may taper in overall width and anteroposterior length in a similar fashion to a natural proximal tibia. Tapered portion 115 is beneficial when a large amount of the natural proximal tibia is resected, thereby requiring a large thickness $T_L$ of platform 114 to maintain the natural joint line of the knee (as discussed above). In addition, referring to FIGS. 2B and 2C, fin windows 128 are substantially smaller than the corresponding fin windows 28 on smaller sized support structure 10, because the larger size of support structure 110 allows for a minimum material thickness to be maintained through more of medullary portion 116 while providing adequate clearance 148 (FIG. 2H) for baseplate fins 120 of larger baseplate 112.

Medullary portions 16, 116 define a truncated, generally conical shape, as described in detail above. However, it is also contemplated that the medullary portion of a support structure in accordance with the present disclosure may have any shape, as required or desired for a particular application.

Figure 3C:
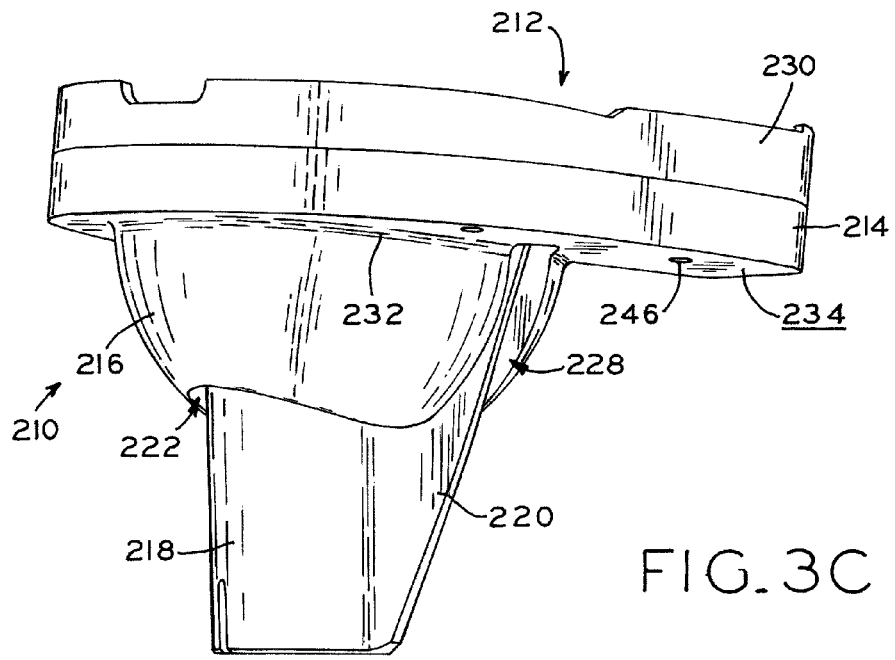
FIG. 3C is another perspective view of the tibial baseplate and support structure shown in FIG. 3A.
Figure 3D:
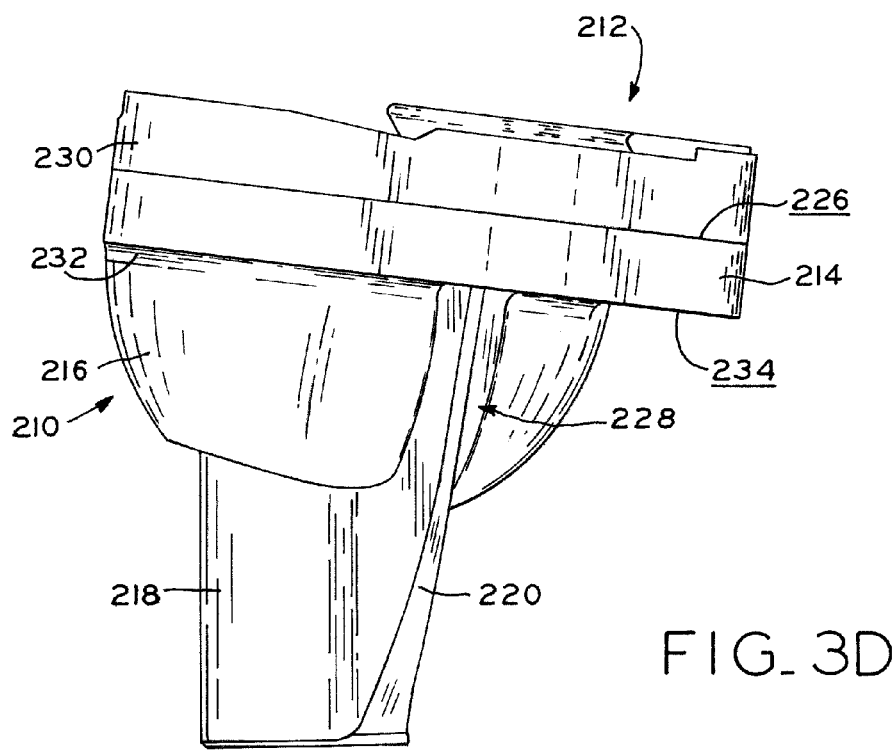
FIG. 3D is a side, elevation view of the tibial baseplate and support structure shown in FIG. 3A.
Figure 3E:
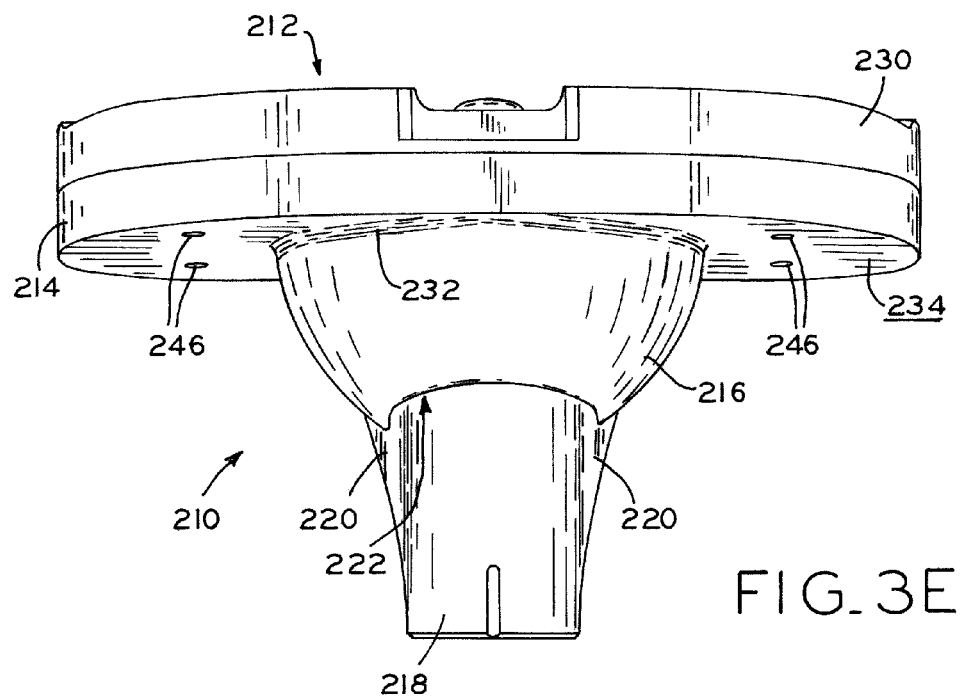
FIG. 3E is an anterior, elevation view of the tibial baseplate and support structure shown in FIG. 3A.
Figure 3F:
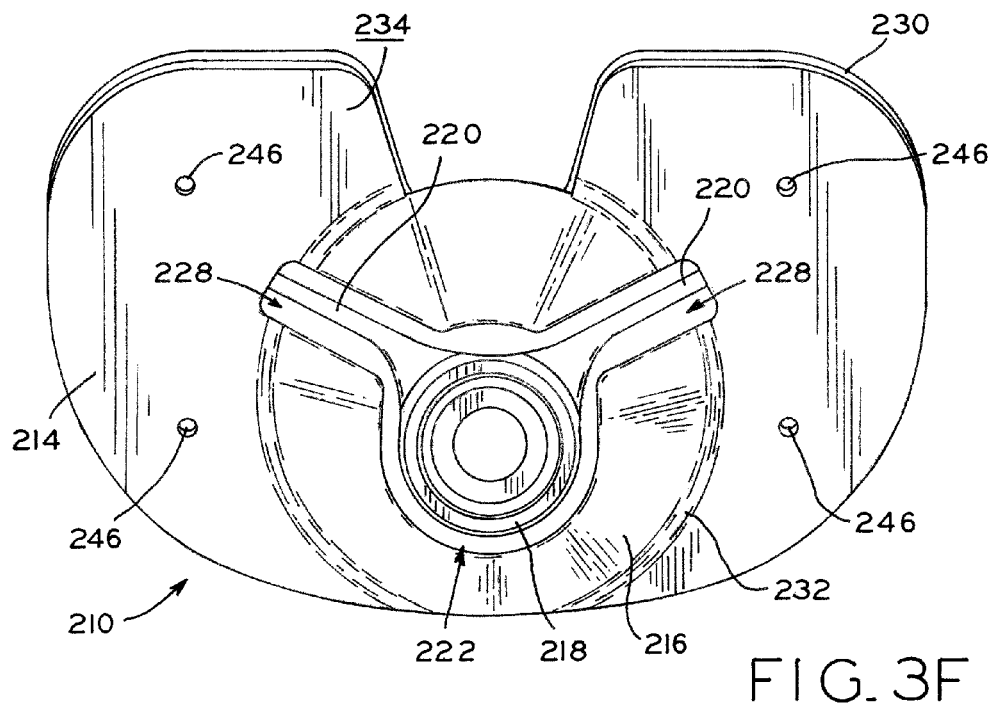
FIG. 3F is a bottom, plan view of the tibial baseplate and support structure shown in FIG. 3A.
Figure 3G:
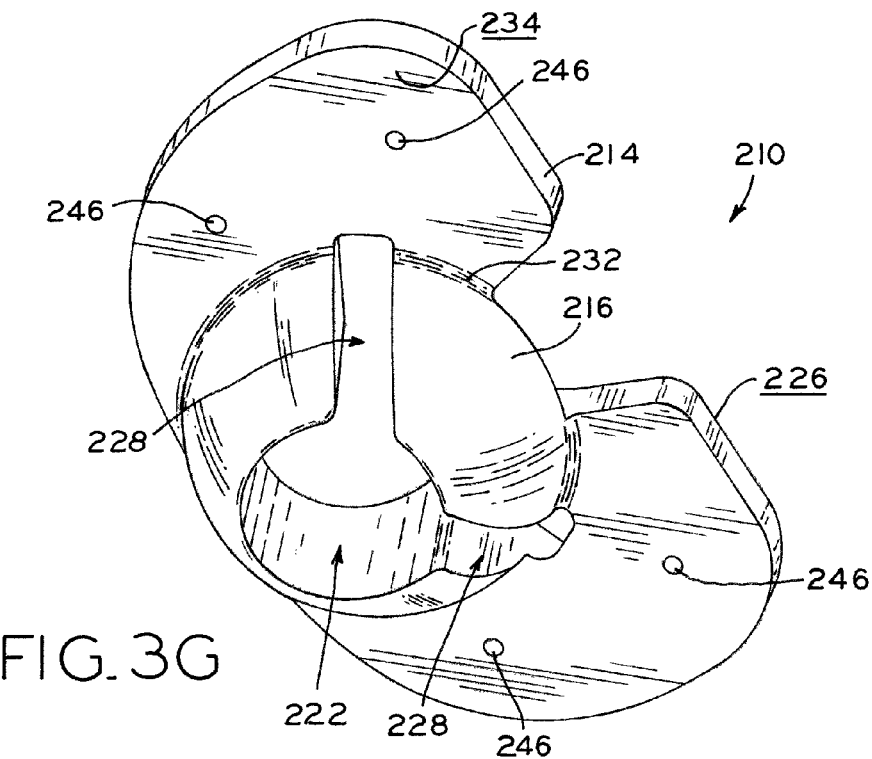
FIG. 3G is a perspective view of the tibial baseplate support structure shown in FIG. 3A.
Figure 3H:
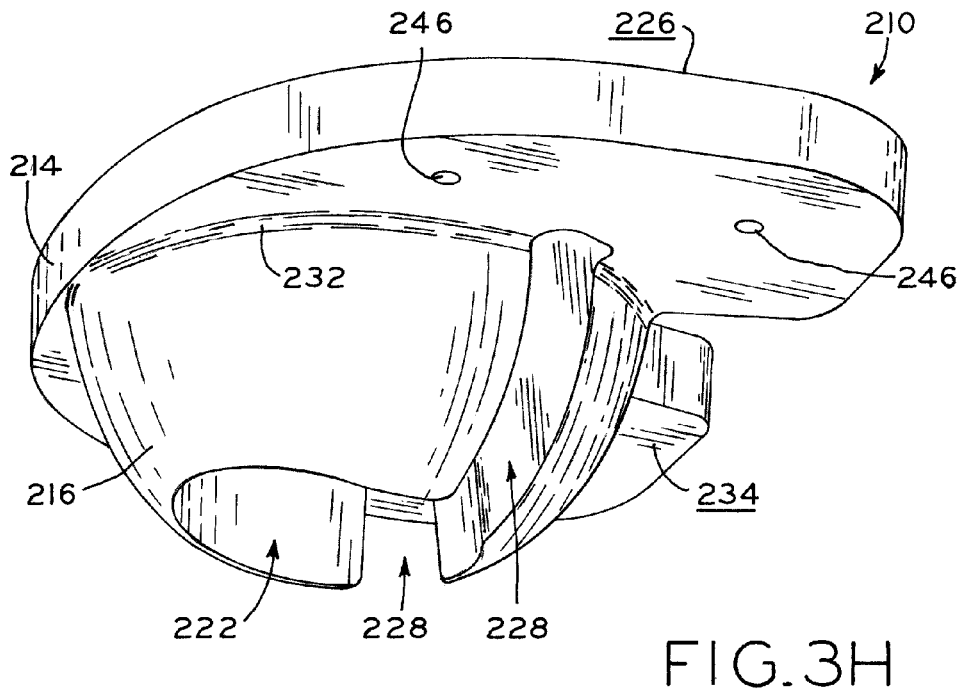
FIG. 3H is another perspective view of the support structure shown in FIG. 3G.

Turning to FIG. 3A, for example, hemispherical support structure 210 includes platform 214, which may be similar to platforms 14 or 114 described above, and hemispherical medullary portion 216. Reference numbers in FIGS. 3A-3H refer to analogous structures described above with respect to support structures 10.

In the illustrative embodiment of FIG. 3A, hemispherical medullary portion 216 includes cutouts 228 in place of fin windows 28, 128 to accommodate fins 220 of tibial baseplate 212, though it is contemplated that the size of hemispherical medullary portion 216 may be expanded to create a window similar to fin windows 28, 128, or may be further expanded to eliminate the need for any fin accommodating window while maintaining a minimum desired material thickness.

As described below, hemispherical medullary portion 216 may be mated with a correspondingly hemispherical cavity created within the tibia. Advantageously, such a hemispherical tibial cavity may be created with standard instruments typically used to prepare the acetabular cavity of a hip to receive an acetabular cup. Such instruments may include acetabular reamers, which are available in sizes small enough to be used with a tibia, such as a diameter as small as 18-20 mm, for example. Spherical support structure 210 may be provided in a wide range of sizes and geometrical configurations to accommodate a correspondingly wide range of anatomical configurations.

Figure 4A:
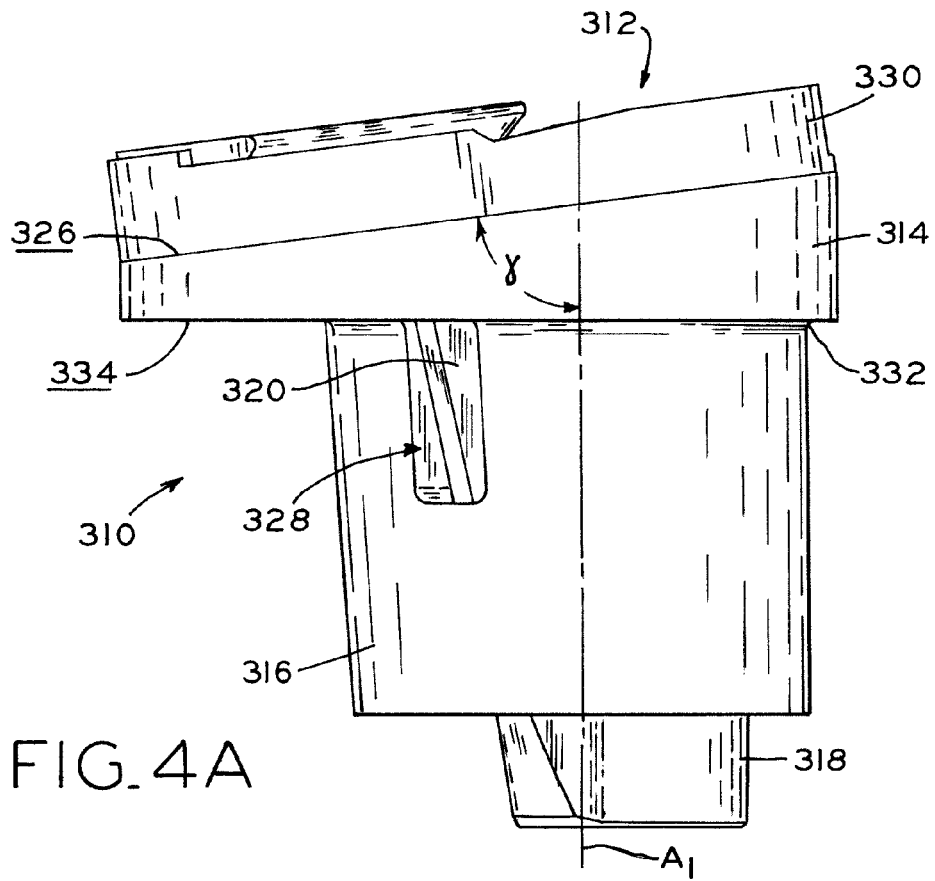
FIG. 4A is a side, elevation view of a tibial baseplate with a tibial baseplate support structure made in accordance with the present disclosure attached thereto, in which the support structure has an angled proximal face.
Figure 4B:
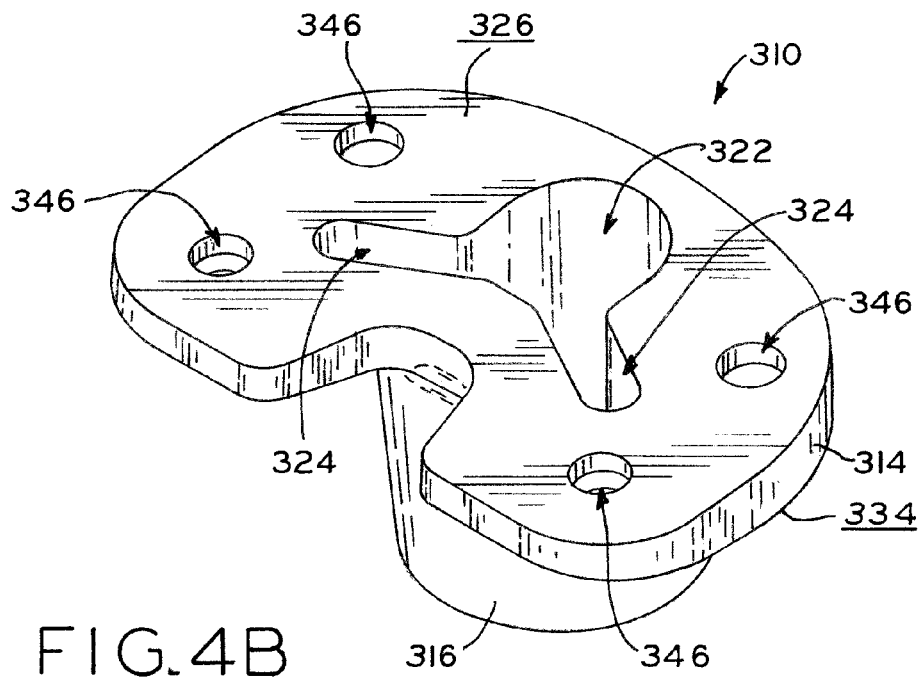
FIG. 4B is a perspective view of the support structure shown in FIG. 4A.
Figure 4C:
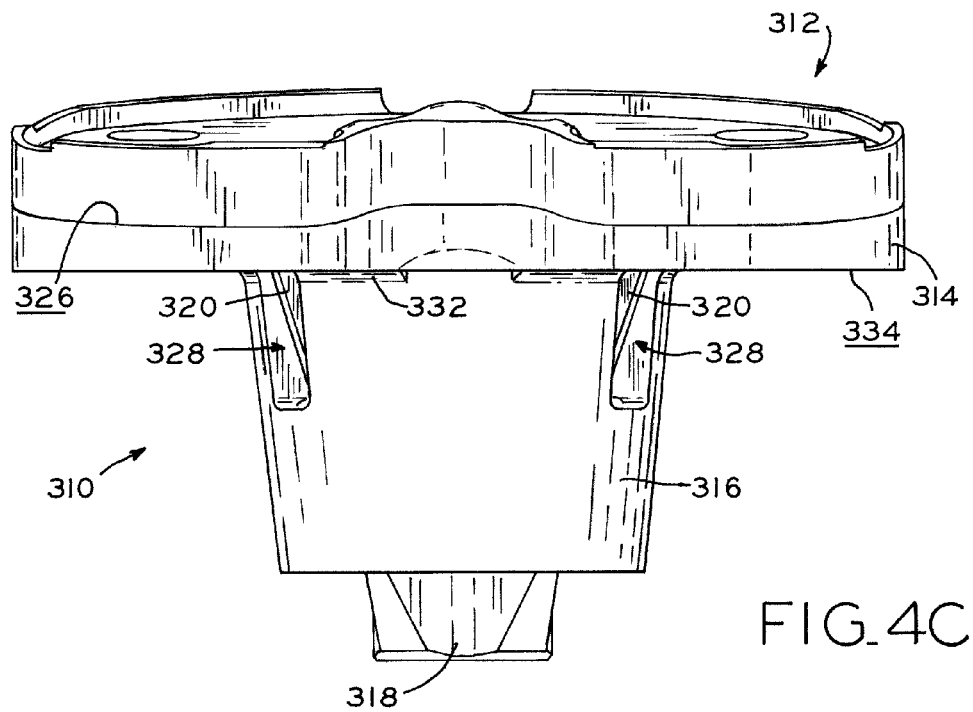
FIG. 4C is a posterior, elevation view of the tibial baseplate and support structure shown in FIG. 4A.
Figure 4D:
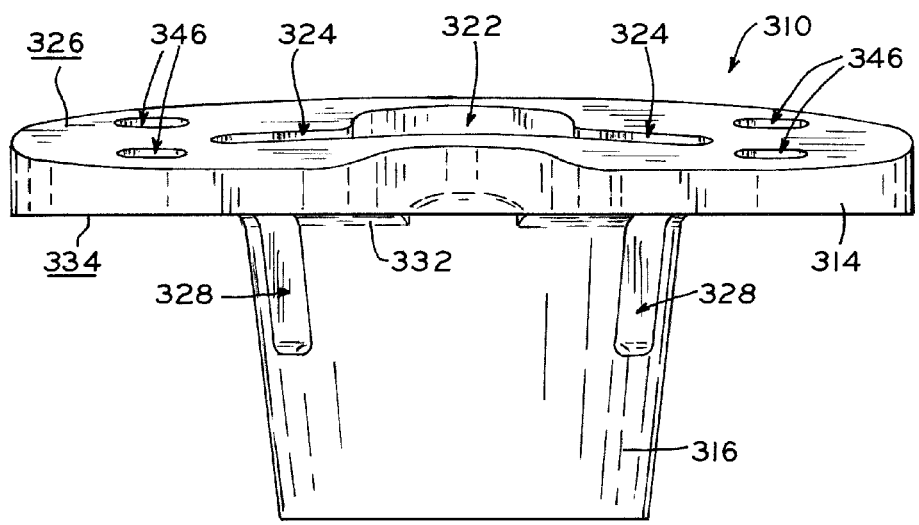
FIG. 4D is a posterior, elevation view of the support structure shown in FIG. 4C.
Figure 4E:
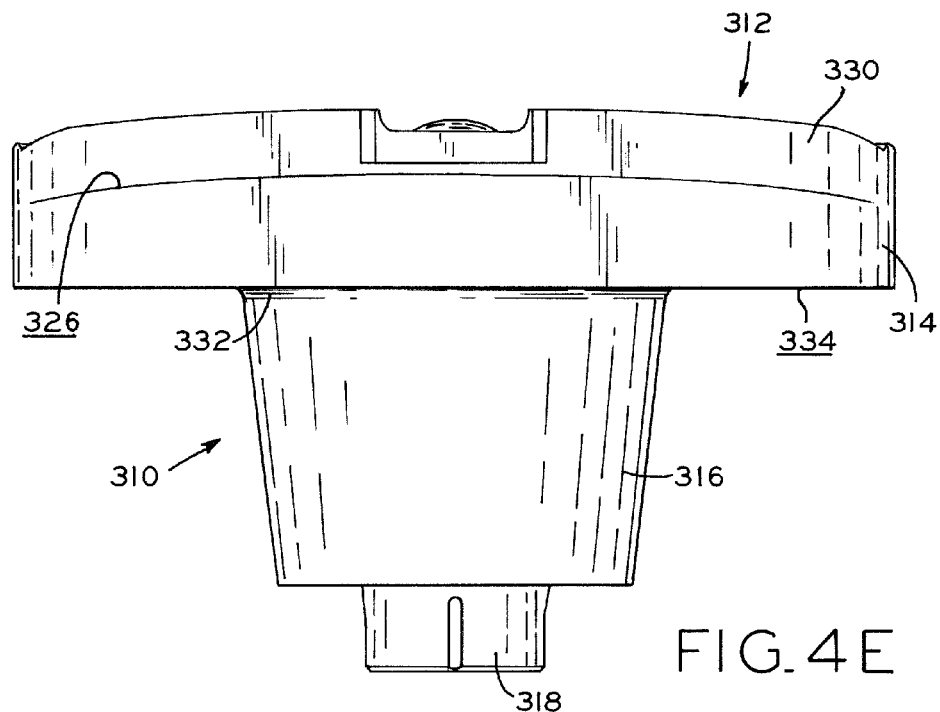
FIG. 4E is an anterior, elevation view of the tibial baseplate and support structure shown in FIG. 4A.
Figure 4F:
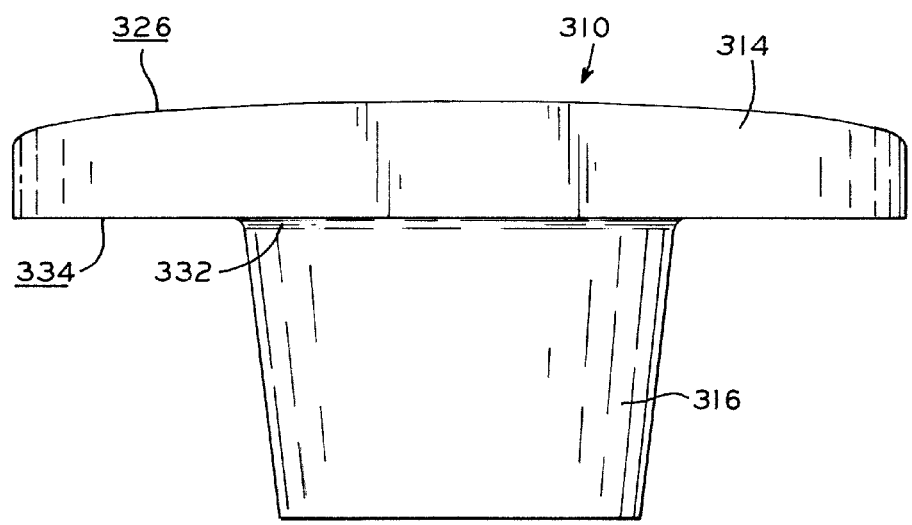
FIG. 4F is an anterior, elevation view of the support structure shown in FIG. 4E.
Figure 5E:
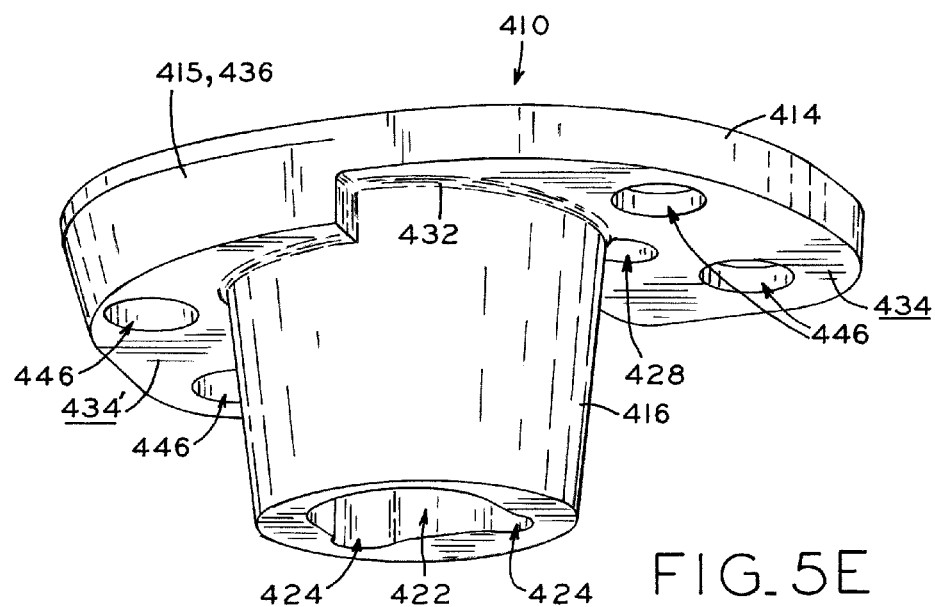
FIG. 5E is another perspective view of the support structure shown in FIG. 5A.
Figure 5F:
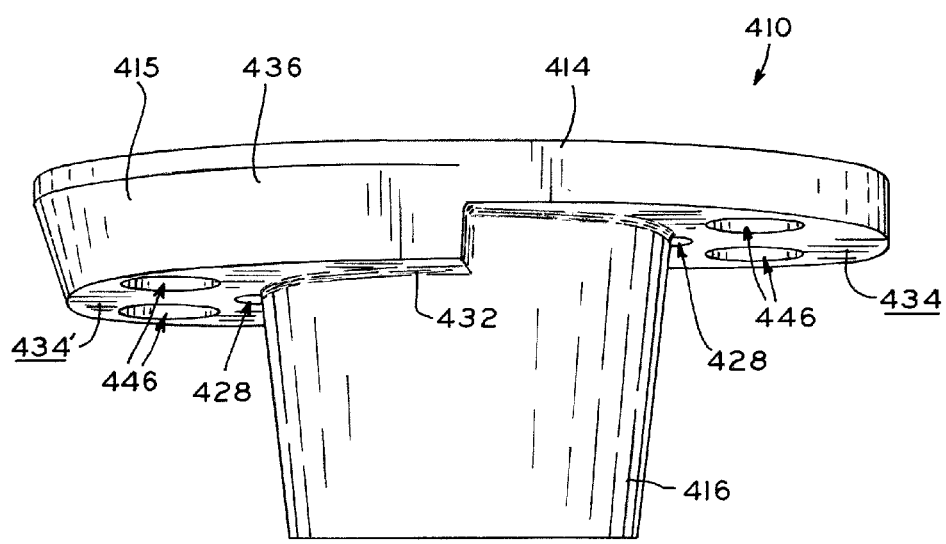
FIG. 5F is an anterior, elevation view of the support structure shown in FIG. 5A.
Figure 6A:
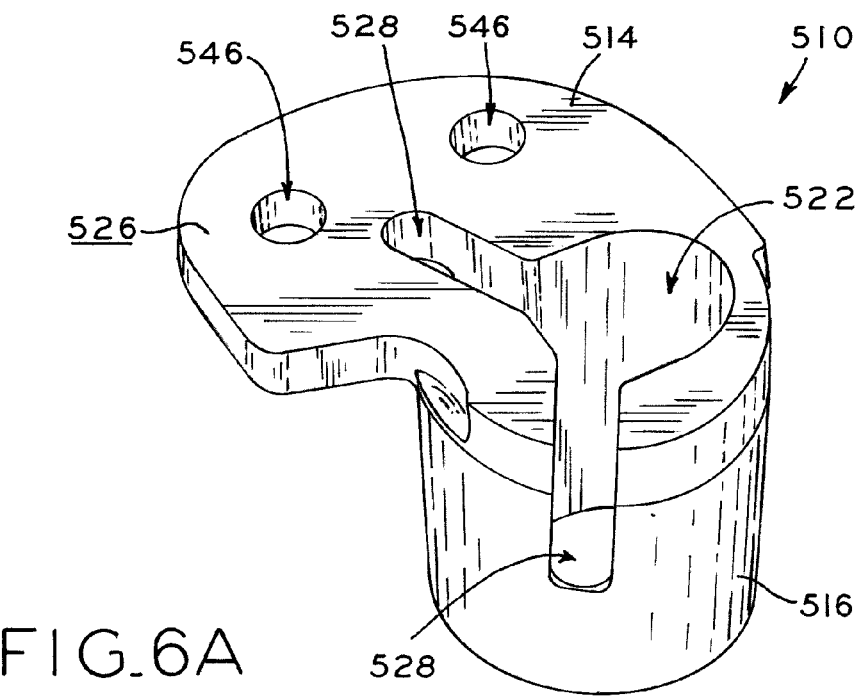
FIG. 6A is a perspective view of a support structure having an asymmetric, single-sided platform portion in accordance with the present disclosure.
Figure 6B:
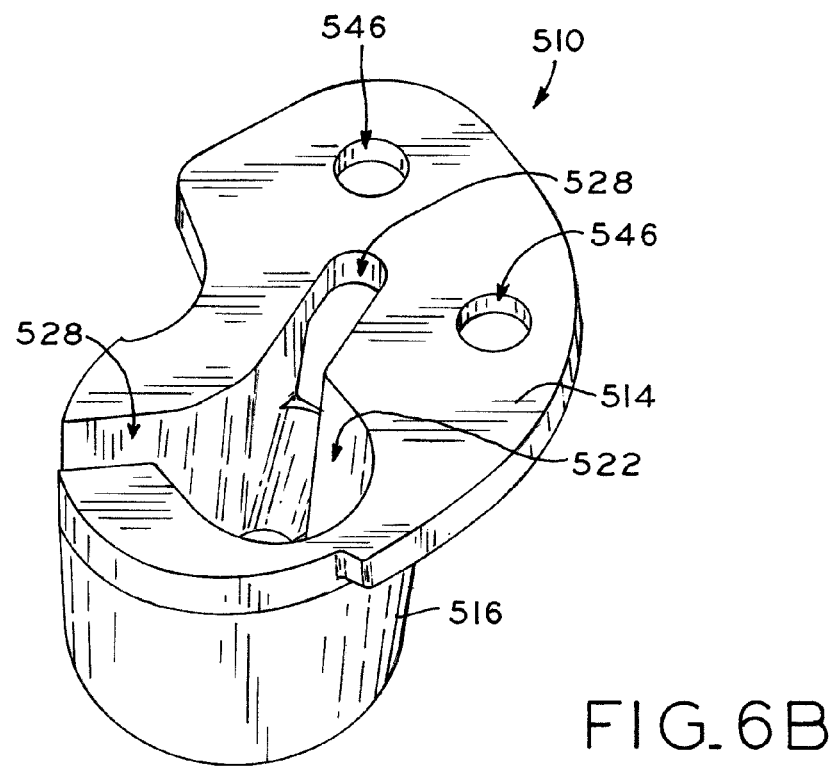
FIG. 6B is another perspective view of the support structure shown in FIG. 6A.
Figure 6E:
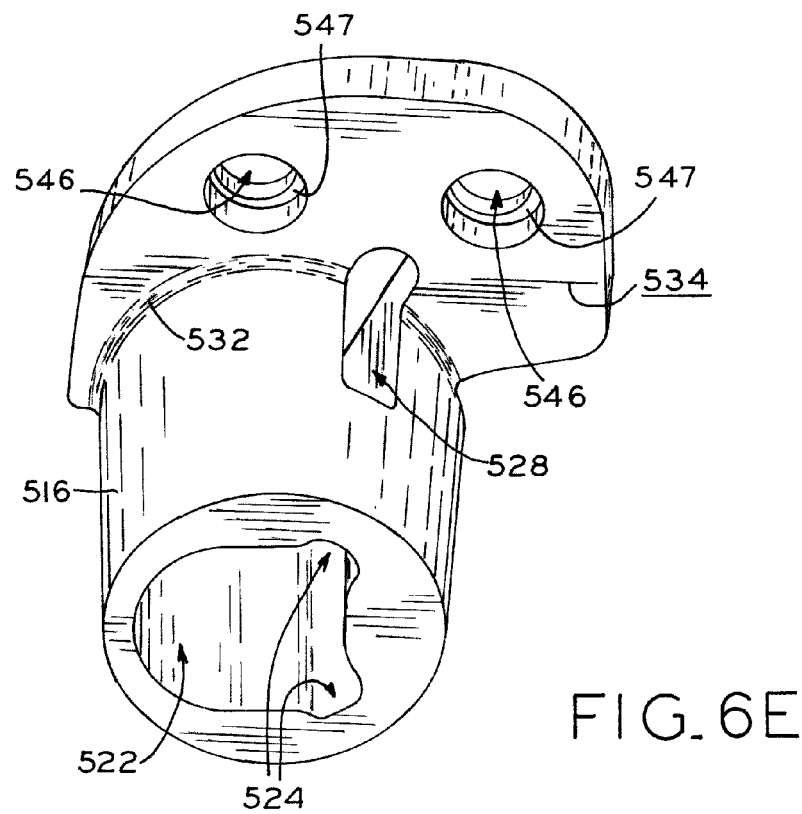
FIG. 6E is another perspective view of the support structure shown in FIG. 6A.
Figure 6F:
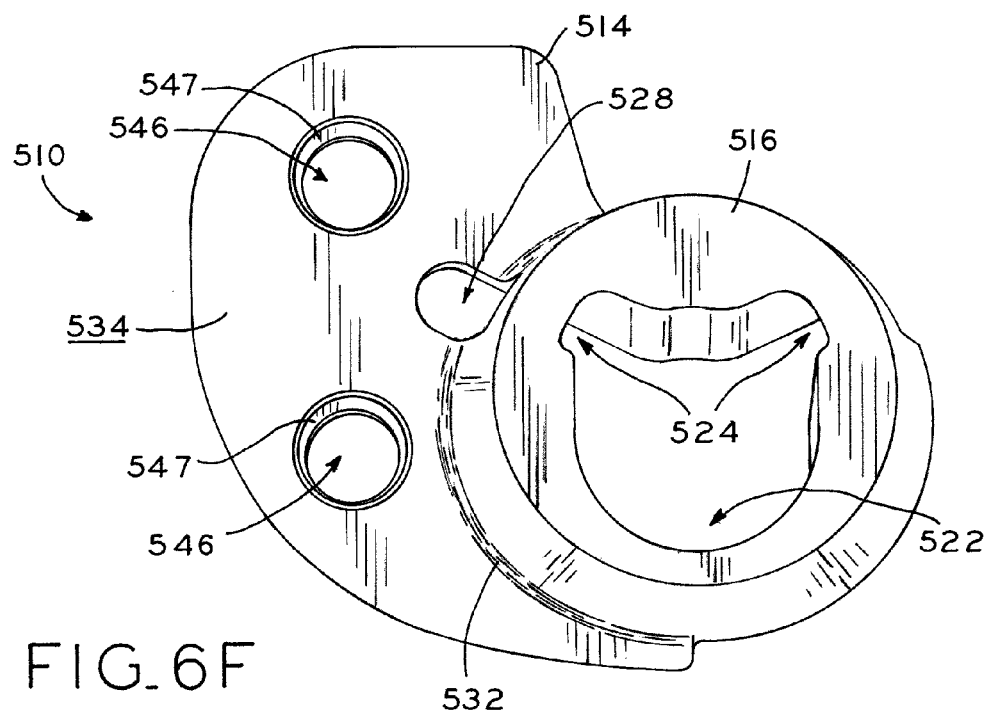
FIG. 6F is a bottom, plan view of the support structure shown in FIG. 6A.
Figure 6G:
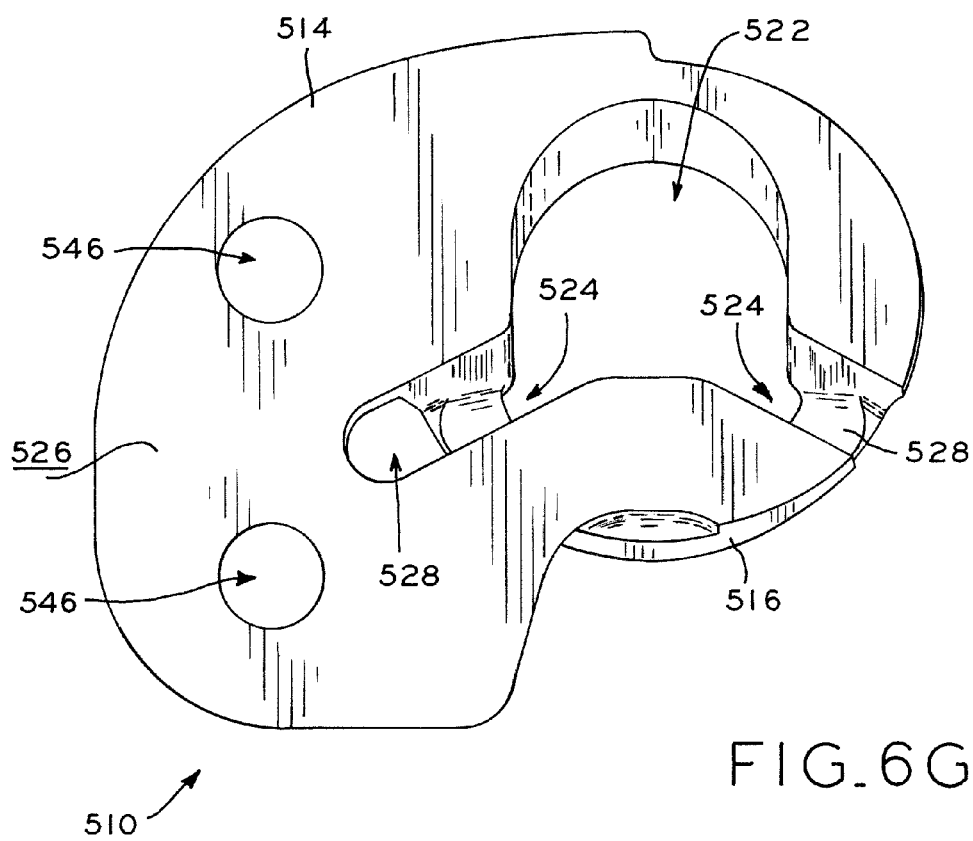
FIG. 6G is a top, plan view of the support structure shown in FIG. 6A.

It is also contemplated that a support structure in accordance with the present disclosure may have other variations in geometry. For example, referring to FIGS. 4A-4F, support structure 310 is illustrated with proximal surface 326 defining an angled profile with respect to axis $A_1$ (FIG. 4A). Reference numbers in FIGS. 4A-4F refer to analogous structures described above with respect to support structures 10.

Angled proximal surface 326 accommodates tibial baseplate 312, which is similarly angled. To create angled proximal surface 326 without disturbing the geometry of medullary portion 316 (which, in the illustrated embodiment, is substantially similar to medullary portion 16 of support structure 10), the thickness of platform portion 314 is varied rather than remaining constant (as thicknesses $T_S$, $T_L$ do as described above). Thus, proximal surface 326 defines angle γ (FIG. 4A) with respect to axis $A_1$. The specific value of angle γ may vary depending on the corresponding angle of proximal portion 230 of tibial baseplate 312, which in turn varies as a function of the chosen anteroposterior angle of the proximal tibial resection performed by a surgeon (i.e., the "tibial slope"). In exemplary embodiments, angle γ may be as little as 0, 3, or 5 degrees, or as large as 7, 10, or 15 degrees, or may be any value within any range defined by the foregoing values. In these exemplary embodiments, angle γ is positive when proximal surface 326 corresponds to a positive tibial slope, which is a slope angled upward along a posterior-to-anterior direction.

In use, one of support structures 10, 110, 210, 310 is implanted upon the proximal tibia when it is determined that portions of the proximal tibial plateau and the metaphyseal and/or diaphyseal bone within the tibia are both damaged and/or diseased, therefore requiring resection. Such bone is resected in a conventional manner, typically with reference to the medullary canal. Additional instrumentation, known to persons having ordinary skill in the art of knee arthroplasty and other orthopaedic surgeries, may be used to orient tibial keel 18, 118, 218 or 318 with respect to the medullary canal of the tibia, such that tibial baseplate 12, 112, 212 or 312 will be properly centered on the resected proximal surface of the tibia when the surgical implantation is complete.

In the metaphyseal and/or diaphyseal portions of the tibia a void is created in the bone to correspond to the geometry of the medullary portion of the chosen support structure (i.e., one of medullary portions 16, 116, 216, 316). In the case of a generally conical medullary portion, such as medullary portions 16, 116, 316, a combination of burrs, mills and/or reamers may be used to create a correspondingly conical medullary void. In the case of a hemispherical medullary portion, such as medullary portion 216, an appropriately sized hemispherical reamer, similar to an acetabular reamer used in hip arthroplasty procedures, may be used to prepare the medullary void. In all cases, the medullary void may be sized for a press-fit of medullary portion 16, 116, 216 or 316, thereby preventing the need for bone cement to aid in the fixation of support structure 10, 110, 210 or 310 to the tibia. As noted above, ingrowth of natural bone into the material of the support structure may be the primary or sole method of fixation between the tibial bone and support structure.

Support structures 10, 110, 210, 310 may be used to restore the joint line of the natural knee where a large amount of the proximal tibia has been resected to remove correspondingly large amounts of diseased, damaged or otherwise defective bone stock. The combination of platforms 14, 114, 214, 314 into a single monolithic structure with medullary portions 16, 116, 216, 316, respectively, ensures that this joint line is maintained over a long period of time by providing a large bone-contacting surface area. In addition, this monolithic combination presents many bone-contacting faces, each of which are oriented in a different direction with respect to the others to yield a "3-dimensional" or multi-faceted profile of bone-contacting faces. This 3-dimensional profile facilitates multidirectional stabilization of the support structure, and of the tibial baseplate mounted thereto, thereby minimizing or eliminating subsidence, anteroposterior movement and medial-lateral movement of the tibial prosthesis in vivo. Moreover, it has been found that the stability provided by a monolithic support structure made in accordance with the present disclosure provides greater stability than would otherwise be provided by a separate tibial cone-shaped implant and a plate-shaped tibial augment implant, whether used in combination or alone.

Advantageously, a support structure made in accordance with the present disclosure does not require the use of cement for fixation to a bone. This lack of cement facilitates bone ingrowth by allowing bone to interdigitate more deeply with the porous bone contacting surfaces of platforms 14, 114, 214, 314 and medullary portions 16, 116, 216, 316. This deep bone ingrowth provides stronger and more secure fixation than could be expected from adhesion between bone cement and bone. Thus, a support structure in accordance with the present disclosure provides a bone replacement and restoration mechanism which gives rise to a stable, bone-like support structure for tibial baseplate components and other associated knee prosthesis components.

Also advantageously, tibial baseplates 12, 112, 212, 312 are removable from support structures 10, 110, 210 in a revision surgery, even if substantial bone ingrowth has occurred between the tibia and support structures 10, 110, 210 or 310. Because no cement is required, as discussed above, cemented fixation between a tibial baseplate and a support structure in accordance with the present disclosure is not required. Rather, mechanical fixation may be used, such as with fastener 40 and nut 42 as detailed above. If a revision surgery is required, such mechanical fixation can be reversed by removing fastener 40 from nut 42, thereby freeing the tibial baseplate from the support structure. The support structure can be left behind, and may therefore remain thoroughly interdigitated with ingrown bone. This remaining support structure obviates the need for removal of any further bone stock during a revision surgery, and provides a reusable, stable and strong support platform for a new tibial baseplate and/or other knee prosthesis components.

Further, the strength of fixation between a support structure in accordance with the present disclosure and the adjacent bone is unexpectedly stronger than other designs adapted for use without bone cement. The monolithic, integral nature of support structures 10, 110, 210, 310 results in a stronger implant as compared to two separate implants separately affixed to the bone. Thus, the overall area of bone ingrowth for support structures 10, 110, 210, 310 is substantially larger than any other similarly sized individual tibial augment structure.

While the disclosure has been described as having exemplary designs, the present disclosure can be further modified within the spirit and scope of this disclosure. This application is therefore intended to cover any variations, uses or adaptations of the disclosure using its general principles. Further, this application is intended to cover such departures from the present disclosure as come within known or customary practice in the art to which this disclosure pertains and which fall within the limits of the appended claims.

What is claimed is:

1. A support structure for use in conjunction with a prosthesis component, the support structure comprising:
    a platform having a proximal surface and a distal surface defining a platform thickness therebetween, said proximal surface and said distal surface cooperating to define a platform outer periphery shaped to correspond with a periphery of a resected proximal tibia, said platform outer periphery defining a platform medial-lateral width and a platform anteroposterior length; and
    a medullary portion extending distally from said distal surface of said platform, said medullary portion monolithically formed with said platform and comprising:
        a medullary portion anteroposterior diameter less than said platform anteroposterior length;
        a medullary portion medial-lateral diameter less than said platform medial-lateral width; and
        a medullary portion height measured along a proximal/distal extent of said medullary portion,
    wherein the support structure provides a longitudinal passage that extends through the support structure from a proximal end opening in the proximal surface of the platform to a distal end opening at a distal end of the medullary portion, the medullary portion including a side wall with an interior surface situated along said longitudinal passage and an exterior surface opposite said interior surface for contacting bone upon implantation, the support structure providing at least a first open window that extends fully through the side wall from said interior surface to said exterior surface, said first open window including a distal window end that terminates proximal of the distal end of the medullary portion.

2. The support structure of claim 1, wherein said monolithically formed platform and medullary portion comprise a porous bone-ingrowth material.

3. The support structure of claim 1, wherein the medullary portion defines a hemispherical shape.

4. The support structure of claim 1, wherein said platform thickness is substantially constant across said platform medial-lateral width and said anteroposterior length.

5. The support structure of claim 1, in combination with a tibial baseplate having a proximal baseplate surface and a distal baseplate surface with a keel extending therefrom, said proximal baseplate surface and said distal baseplate surface cooperating to define a tibial baseplate periphery corresponding to said platform outer periphery, and said keel extending through the longitudinal passage and protruding from the distal end opening at the distal end of said medullary portion.

6. The combination of claim 5, wherein said monolithically formed platform and medullary portion are formed with a porous bone-ingrowth metallic material.

7. The combination of claim 5, further comprising means for mechanically attaching said support structure to said tibial baseplate.

8. The combination of claim 5, wherein:

said tibial baseplate comprises at least a first fin extending radially outwardly from said keel and oriented such that the first fin extends down a side of the keel; and said first open window formed at a junction between said medullary portion and said platform, said first open window sized and positioned to provide clearance for said first fin of said tibial baseplate.

9. The combination of claim 8, wherein said first open window maintains a minimum thickness of the material of said support component of at least 1 mm.

10. The combination of claim 5, wherein said longitudinal passage is sized to receive said keel of said tibial baseplate with clearance between said interior surface and an outer peripheral wall of said keel.

11. The support structure of claim 1, wherein:

said medullary portion defines a central longitudinal axis extending along the proximal/distal extent thereof; and said exterior surface of the side wall of said medullary portion defines a tapered outer surface such that a medial boundary and a lateral boundary of said medullary portion each define a taper angle with respect to said central longitudinal axis, said taper angle between 4 degrees and 15 degrees.

12. The support structure of claim 11, wherein a posterior boundary of said medullary portion defines a posterior taper angle with respect to said central longitudinal axis, said posterior taper angle between 10 and 19 degrees.

13. The support structure of claim 11, wherein an anterior boundary of said medullary portion is substantially parallel to said central longitudinal axis.

14. A proximal tibial implant system, comprising:

a proximal tibial implant including a tibial baseplate with a proximal baseplate surface and a distal baseplate surface with a keel extending therefrom, said proximal tibial implant including at least a first fin extending down a side of the keel from the distal baseplate surface to a distal end of the keel; and a support structure for use in conjunction with the proximal tibial implant, the support structure formed with a porous bone-ingrowth metallic material and comprising:

a platform having a proximal surface and a distal surface defining a platform thickness therebetween, said proximal surface and said distal surface cooperating to define a platform outer periphery shaped to correspond with a periphery of a resected proximal tibia, said periphery divided into a medial side and an opposing lateral side, said platform outer periphery defining a platform medial-lateral width and a platform anteroposterior length; and a medullary portion extending distally from said distal surface of said platform and from at least one of said medial side and said lateral side, said medullary portion monolithically formed with said platform and comprising:

a medullary portion anteroposterior diameter less than said platform anteroposterior length;

a medullary portion medial-lateral diameter; and a medullary portion height measured along a proximal/distal extent of said medullary portion, wherein the support structure provides a longitudinal passage that extends through the support structure from a proximal end opening in the proximal surface of the platform to a distal end opening at a distal end of the medullary portion, said keel extending through the longitudinal passage and protruding from the distal end opening at the distal end of said medullary portion.

15. The proximal tibial implant system of claim 14, wherein said distal surface of said platform is stepped, such that said platform thickness is larger at one of said medial side and said lateral side as compared to the other of said medial side and said later side.

16. The proximal tibial implant system of claim 14, wherein the thicker of said medial side and said lateral side comprises a tapered outer surface extending distally, such that said periphery is defined at said proximal surface of said platform for the thicker of said medial side and said lateral side.

17. The proximal tibial implant system of claim 14, wherein said platform occupies only one of said medial side and lateral side, whereby said support structure is designed to augment only one side of the resected proximal tibia.

18. The proximal tibial implant system of claim 14, wherein the medullary portion includes a side wall with an interior surface situated along said longitudinal passage and an exterior surface opposite said interior surface for contacting bone upon implantation, the support structure providing at least a first open window that extends fully through the side wall from said interior surface to said exterior surface.

19. The proximal tibial implant system of claim 18, wherein the first open window includes a distal window end that terminates proximal of the distal end of the medullary portion.

20. The proximal tibial implant system of claim 18, wherein said first open window spans a junction formed between said medullary portion and said platform.

21. The proximal tibial implant system of claim 18, wherein a clearance space exists between said first open window and said first fin.

22. The proximal tibial implant system of claim 21, wherein said first fin extends through said first open window so as to protrude from the exterior surface of said side wall.

* * * * *

UNITED STATES PATENT AND TRADEMARK OFFICE
CERTIFICATE OF CORRECTION

PATENT NO. : 8,900,317 B2  
APPLICATION NO. : 13/475721  
DATED : December 2, 2014  
INVENTOR(S) : Zubok et al.

Page 1 of 1

It is certified that error appears in the above-identified patent and that said Letters Patent is hereby corrected as shown below:

In The Claims

In column 18, line 27, in Claim 15, delete "later" and insert --lateral--, therefor In column 18, line 36, in Claim 17, after "and", insert --said--, therefor Signed and Sealed this
Seventeenth Day of March, 2015

Michelle K. Lee
*Director of the United States Patent and Trademark Office*